(12) United States Patent
Don Michael et al.

(10) Patent No.: US 7,214,237 B2
(45) Date of Patent: *May 8, 2007

(54) VASCULAR FILTER WITH IMPROVED STRENGTH AND FLEXIBILITY

(76) Inventors: T. Anthony Don Michael, 4109 Sill Pl., Bakersfield, CA (US) 93306; Peter Besselink, Gronausestraat 1220, Enschede (NL) 7534 AT ( * ) Notice: Subject to any disclaimer, the term of this patent is extended or adjusted under 35 U.S.C. 154(b) by 258 days.

This patent is subject to a terminal disclaimer.

(21) Appl. No.: 10/304,067

(22) Filed: Nov. 26, 2002
(Under 37 CFR 1.47)

(65) Prior Publication Data
US 2003/0153943 A1    Aug. 14, 2003

Related U.S. Application Data

(63) Continuation-in-part of application No. 09/803,641, filed on Mar. 12, 2001, now Pat. No. 6,485,502.

(60) Provisional application No. 60/412,071, filed on Sep. 19, 2002, provisional application No. 60/417,408, filed on Oct. 9, 2002.

(51) Int. Cl.
*A61M 29/00* (2006.01)

(52) U.S. Cl. .................................. 606/200
(58) Field of Classification Search ............ 606/200, 606/113, 114, 108; 623/1.11
See application file for complete search history.

(56) References Cited

U.S. PATENT DOCUMENTS

| | | | |
|---|---|---|---|
| 3,874,388 A | * | 4/1975 | King et al. ............... 606/232 |
| 4,425,908 A | | 1/1984 | Simon |
| 4,619,246 A | | 10/1986 | Molgaard-Nielsen et al. |
| 4,867,742 A | | 9/1989 | Calderon |
| 4,911,163 A | | 3/1990 | Fina |
| 5,108,419 A | | 4/1992 | Reger et al. |
| 5,626,605 A | | 5/1997 | Irie et al. |
| 5,833,644 A | | 11/1998 | Zadno-Azizi et al. |

(Continued)

FOREIGN PATENT DOCUMENTS

DE    4101935    *    7/1992

(Continued)

OTHER PUBLICATIONS

Translation of Patent DE 4101935, Intravascular Valve, Jul. 1992, Matthias Fischer et al.*

*Primary Examiner*—Anhtuan T. Nguyen
*Assistant Examiner*—Elizabeth Houston
(74) *Attorney, Agent, or Firm*—Browdy and Neimark, PLLC

(57) ABSTRACT

A medical device, such as a vascular filter, composed of: a reinforced membrane unit composed of: a thin filter membrane; and fibers of reinforcement material embedded in the membrane to strengthen the filter and securely attach the fibers to the membrane.

A method of fabricating the filter by the steps of: providing a mold that can be melted, dissolved, or deformed without damaging membrane material; covering the mold with an intermediate material that is easily separated from the membrane material; covering the intermediate material with the membrane material; placing the fibers in contact with the membrane material that covers the intermediate material; covering the fibers with additional membrane material to form the membrane with embedded fibers; removing the mold by melting, dissolving, or deforming the mold; and removing the intermediate material from the membrane.

5 Claims, 15 Drawing Sheets

U.S. PATENT DOCUMENTS

| | | |
|---|---|---|
| 5,833,650 A | 11/1998 | Imran |
| 5,885,258 A | 3/1999 | Sachdeva et al. |
| 5,997,562 A | 12/1999 | Zadno-Azizi et al. |
| 6,013,093 A | 1/2000 | Nott et al. |
| 6,022,336 A * | 2/2000 | Zadno-Azizi et al. .. 604/101.05 |
| 6,053,932 A | 4/2000 | Daniel et al. |
| 6,203,561 B1 * | 3/2001 | Ramee et al. ............... 606/200 |
| 6,364,895 B1 | 4/2002 | Greenhalgh |
| 6,485,502 B2 * | 11/2002 | Don Michael et al. ..... 606/200 |
| 6,582,448 B1 * | 6/2003 | Boyle et al. ................ 606/200 |
| 6,602,271 B2 * | 8/2003 | Adams et al. .............. 606/200 |
| 6,692,513 B2 * | 2/2004 | Streeter et al. ............. 606/200 |

FOREIGN PATENT DOCUMENTS

| | | |
|---|---|---|
| DE | 4101935 A1 | 7/1992 |
| WO | WO 9916362 A1 | 4/1999 |
| WO | WO 9944542 A2 | 9/1999 |
| WO | WO 0108743 A1 | 2/2001 |

* cited by examiner

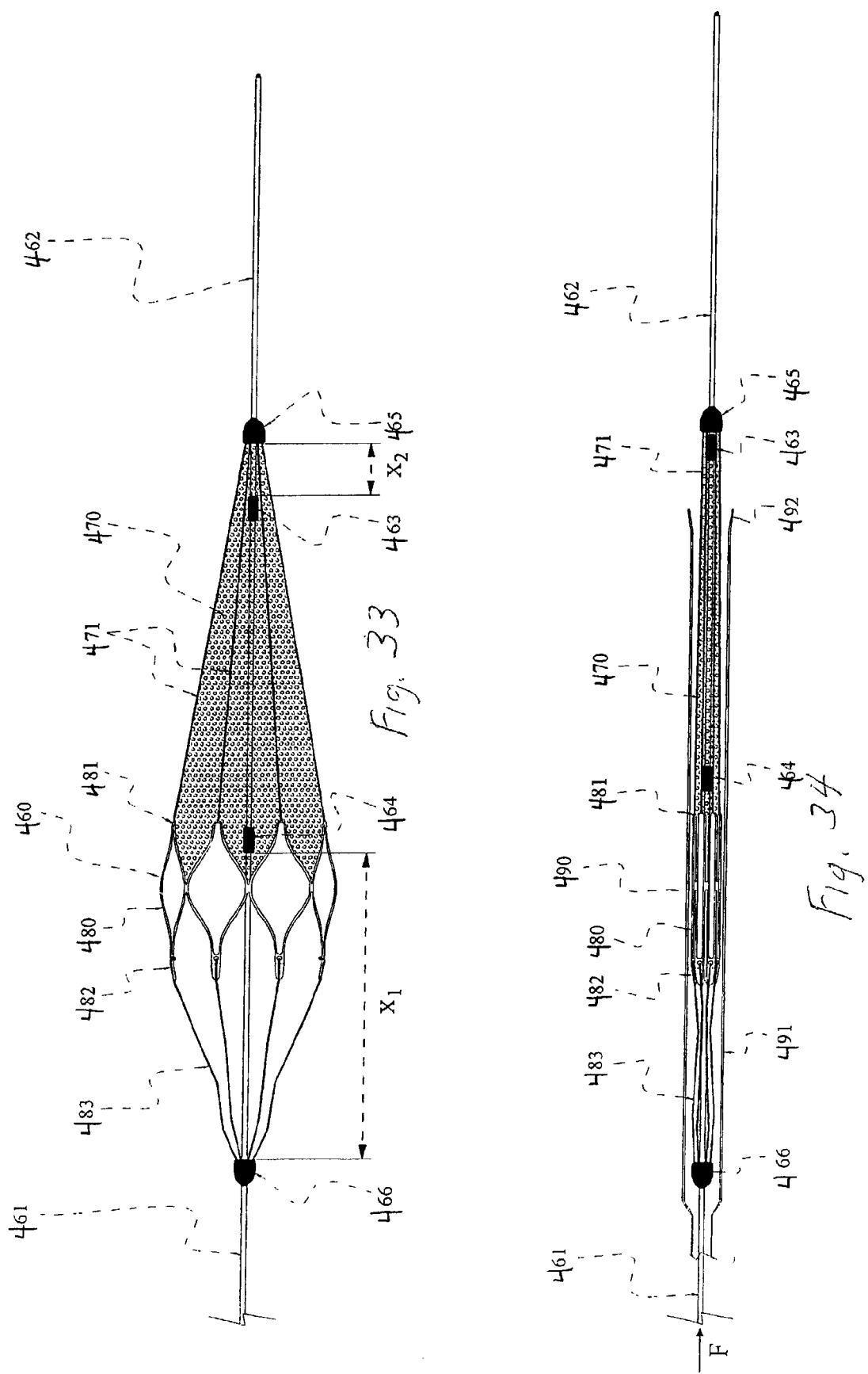

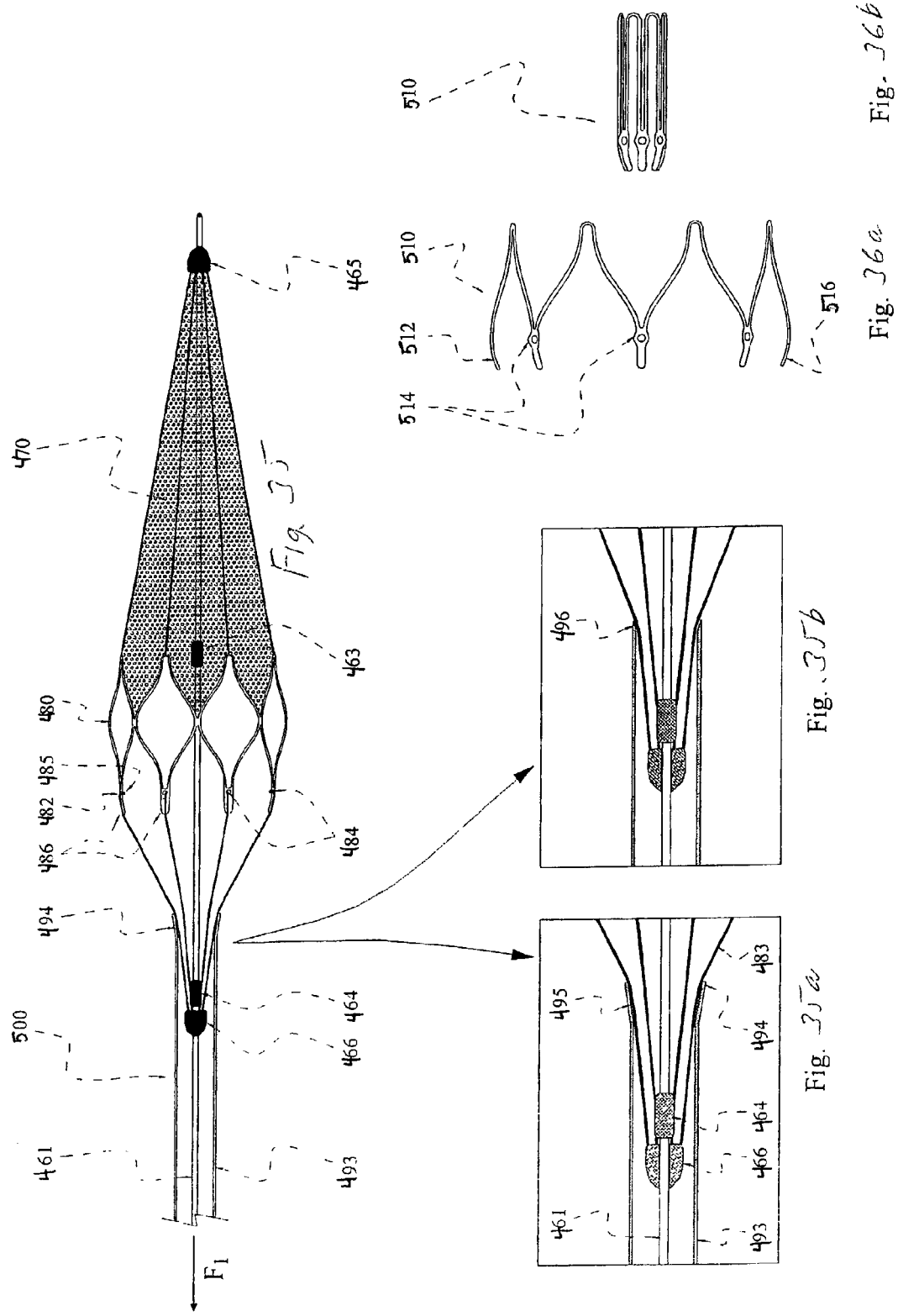

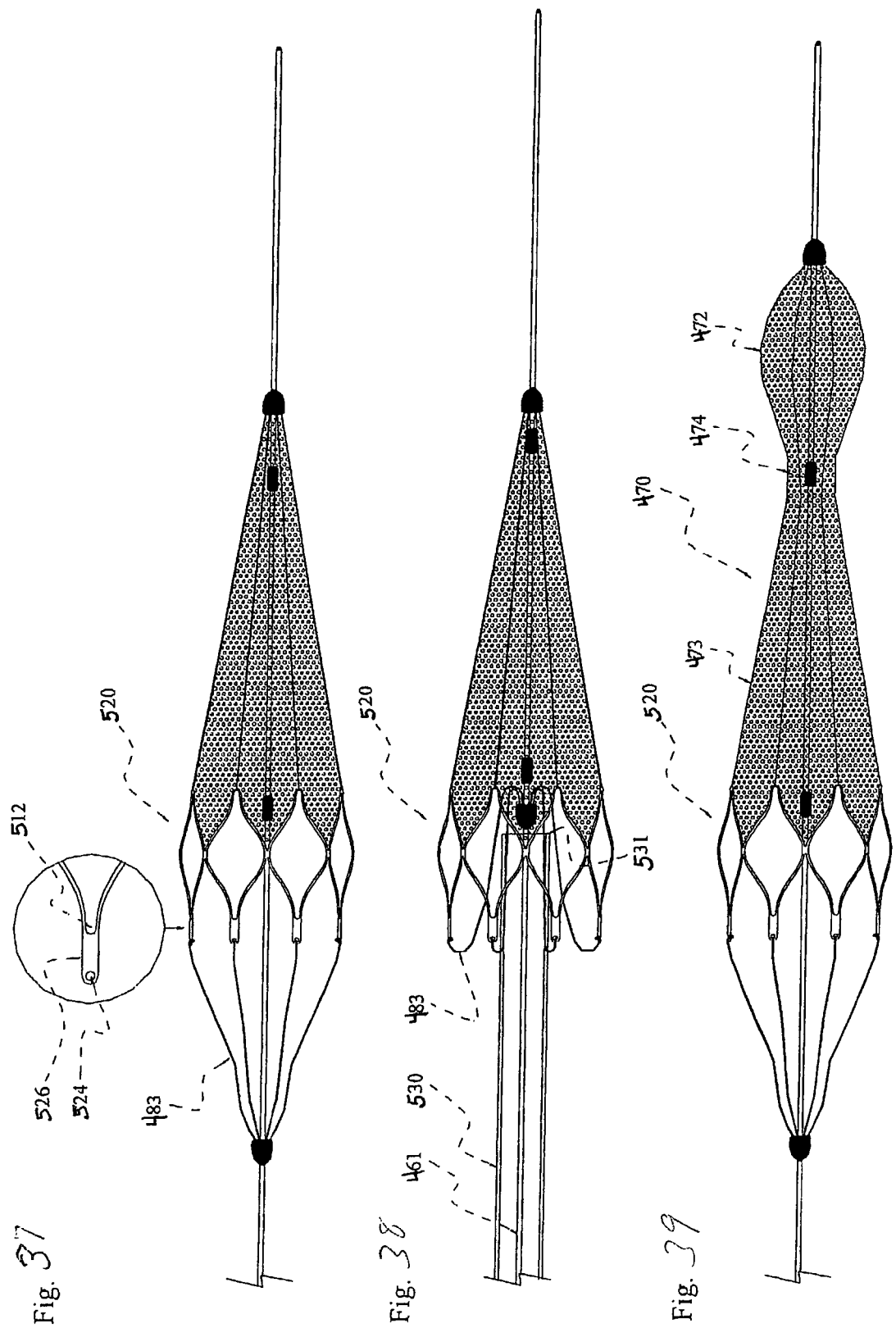

VASCULAR FILTER WITH IMPROVED STRENGTH AND FLEXIBILITY

This is a continuation-in-part of allowed U.S. application Ser. No. 09/803,641, filed on Mar. 12, 2001, now U.S Pat. No. 6,485,502, the entire disclosure of which is incorporated herein by reference. This application also claims the benefit of the filing dates of the following U.S. Provisional Applications: No. 60/412,071, filed Sep. 19, 2002; No. 60/417,408, filed Oct. 9, 2002.

BACKGROUND OF THE INVENTION

This invention relates to medical devices, such as vascular filters to be used in a body lumen, such as a blood vessel, with improved strength and flexibility. A filter according to the invention includes a proximal frame section, a distal section and a flexible thin membrane with perfusion holes of a diameter that allows blood to pass, but prevents the movement of emboli downstream.

Both sections can be collapsed into a small diameter delivery catheter and expanded upon release from this catheter. The membrane has a proximal entrance mouth, which can be expanded, or deployed, substantially to the same size as the body lumen. It is attached to the proximal frame section, which has the function to keep the mouth of the membrane open and prevent the passing of emboli between the body lumen wall and the edge of the filter mouth.

In order to have a good flexibility, the membrane is made extremely thin. Normally this would create the risk that the membrane could tear easily, which could cause problems because emboli and pieces of the membrane would then be carried downstream from the filter site.

U.S. Pat. No. 5,885,258 discloses a retrieval basket for catching small particles, made from a slotted tube preferably made of Nitinol, a titanium nickel shape memory alloy. The pattern of the slots allows expansion of the Nitinol basket and by shape setting (heat treatment in the desired unconstrained geometry) this basket is made expandable and collapsible by means of moving it out or into a surrounding delivery tube.

In principle, a distal filter is made of such an expandable frame that defines the shape and enables placement and removal, plus a filter membrane or mesh that does the actual filtering work.

Sometimes the expandable frame and the mesh are integrated and made from a single material, for example Nitinol, as disclosed in U.S. Pat. No. 6,383,205 or U.S. Published Application No. 2002/0095173. These filters do not have a well-defined and constant size of the holes where the blood flows through, because of the relative movement of the filaments in the mesh. This is a disadvantage, because the size of emboli can be very critical, e.g. in procedures in the carotid arteries. Further the removal of such a filter, accompanied by a reduction of the diameter, may be critical because emboli can be squeezed through the mesh openings with their changing geometry.

A much better control of the particle size is achieved with a separate membrane or filter sheath, which has a well-defined hole pattern with for example holes of 100 microns, attached to a frame that takes care of the correct placement and removal of the filter.

WO 00/67668 discloses a Nitinol basket that forms the framework of the filter, and a separate polymer sheath is attached around this frame. At the proximal side, the sheath has large entrance ports for the blood and at the distal side a series of small holes filters out the emboli. This system, however, has some major disadvantages. First of all, the closed basket construction makes this filter frame rather rigid and therefore it is difficult to be used in tortuous arteries. At a curved part of an artery, it may even not fit well against the artery wall and will thus cause leakage along the outside of the filter.

Another disadvantage of such filters is there is a high risk of squeezing-out the caught debris upon removal, because the struts of the framework force the debris back in the proximal direction, while the volume of the basket frame decreases when the filter is collapsed. Further the construction makes it very difficult to reduce the profile upon placement of the filter. This is very critical, because these filters have to be advanced through critical areas in the artery, where angioplasty and/or stenting are necessary. Of course the catheter that holds this filter should be as small as possible then. In the just described filter miniaturization would be difficult because at a given cross section there is too much material. The metal frame is surrounded by polymer and in the center there is also a guide wire. During angioplasty and stenting, the movements of the guide wire will create further forces that influence the position and shape of the filter, which may cause problems with the proper sealing against the artery wall. This is also the case in strongly curved arteries.

In U.S. Pat. No. 6,348,062, a frame is placed proximal and a distal polymer filter membrane has the shape of a bag, attached to one or more frame loops, forming an entrance mouth for the distal filter bag. Here the bag is made of a very flexible polymer and the hole size is well defined. Upon removal, the frame is closed, thus closing the mouth of the bag and partly preventing the squeezing-out of debris. This is already better than for the full basket design, which was described above, where the storage capacity for debris of the collapsed basket is relatively small. The filter bag is attached to the frame at its proximal end and sometimes to a guide wire at its distal end. Attachment to the guide wire can be advantageous, because some pulling force may prevent bunching of the bag in the delivery catheter.

It may be clear that it is easier to pull a flexible folded bag through a small diameter hole, than to push it through. However, the deformation of the bag material should stay within certain limits.

If the filter is brought into a delivery sheath of small diameter, collapsing the frame and pulling the bag into the delivery sheath causes rather high forces on the connection sites of filter to frame and/or guide wire. While the metal parts of the frame slide easily through such a delivery sheath, the membrane material may have the tendency to stick and in the worst case it may even detach from the frame and tear upon placement or during use, because of too much friction, unlimited expansion, crack propagation etc.

The connection of the filter bag to the frame is rather rigid, because of the method of direct attachment. Additional flexibility, combined with a high strength attachment spot would also be advantageous.

Methods for making kink resistant reinforced catheters by embedding wire ribbons are described in PCT/US93/01310. There, a mandrel is coated with a thin layer of encapsulating material. Then, a means (e.g. a wire) for reinforcement is deposited around the encapsulating material and eventually a next layer of encapsulating material is coated over the previous layers, including the reinforcement means. Finally the mandrel is removed from the core of the catheter.

Materials for encapsulating are selected from the group consisting of polyesterurethane, polyetherurethane, aliphatic polyurethane, polyimide, polyetherimide, polycarbonate, polysiloxane, hydrophilic polyurethane, polyvinyls, latex and hydroxyethylmethacrylate.

Materials for the reinforcement wire are stainless steel, MP35, Nitinol, tungsten, platinum, Kevlar, nylon, polyester and acrylic. Kevlar is a Dupont product, made of long molecular higly oriented chains, produced from polyparaphenylene terephalamide. It is well known for its high tensile strength and modulus of elasticity.

In U.S. application Ser. No. 09/537,461 the use of polyethylene with improved tensile properties is described. It is stated that high tenacity, high modulus yarns are used in medical implants and prosthetic devices. Properties and production methods for polyethylene yarns are disclosed.

U.S. Pat. No. 5,578,374 describes very low creep, ultra high modulus, low shrink, high tenacity polyolefin fibers having good strength retention at high temperatures, and methods to produce such fibers. In an example, the production of a poststretched braid, applied in particularly woven fabrics is described.

In U.S. Published Application No. 2001/0034197, oriented fibers are used for reinforcing an endless belt, comprising a woven or non-woven fabric coated with a suitable polymer of a low hardness polyurethane membrane, in this case to make an endless belt for polishing silicon wafers. Examples are mentioned of suitable yarns like meta- or para-aramids such as KEVLAR, NOMEX OR TWARON; PBO or its derivatives; polyetherimide; polyimide; polyetherketone; PEEK; gel-spun UHMW polyethylene (such as DYNEEMA or SPECTRA); or polybenzimidazole; or other yarns commonly used in high-performance fabrics such as those for making aerospace parts. Mixtures or blends of any two or more yarns may be used, as may glass fibers (preferably sized), carbon or ceramic yarns including basalt or other rock fibers, or mixtures of such mineral fibers with synthetic polymer yarns. Any of the above yarns may be blended with organic yarns such as cotton.

The present invention further relates to medical procedures performed in blood vessels, particularly in arteries.

This invention relates more specifically to systems and methods involving angioplasty and/or stenting, where protection against loose embolic material is a major concern.

Such procedures are performed to remove obstructions or blockages in arteries and thereby alleviate life-threatening conditions. The procedures currently employed result in a fracturing or disintegration of the obstructing material and if the resulting particles, or debris, were permitted to flow downstream within the circulatory system, they would be likely to cause blockages in smaller arteries, or their microscopic branches termed the microcirculation, downstream of the treatment site. The result can be new life-threatening conditions, including stroke.

Various systems and techniques have already been proposed for removing this debris from the circulatory system in order to prevent the debris from causing any harm. These techniques involve temporarily obstruction the artery, at a location downstream of the obstruction, by means of an element such as a balloon, and then suctioning debris and blood from the treatment site. While such techniques can effectively solve the problem stated above, they require that blood flow through the artery be obstructed, causing complete cessation or at least a substantial reduction in blood flow volume, during a time period which can be significant for organ survival for example, the time limit for the brain is measured in seconds and for the heart, in minutes.

Although filters have been used, they suffer from the limitation of either obstructing flow or allowing micro embolism due to fixed pore size. Furthermore, the collected debris can reflux out of the filter when it is closed and lead to embolism. Upon pulling back of a basket/filter with entrapped particles into a delivery catheter, debris particles may be squeezed out of the device, because the volume is strongly reduced. During this pulling back, the filter no longer covers the full cross-section of the artery, so particles that are squeezed out then can freely flow around the outer edge of the filter and move distally through the artery.

The invention also relates to a combined delivery/post-dilatation device for self-expanding stents.

Normally the delivery of self-expanding stents is done with a separate delivery sheath, which is pulled back to release the compressed stent from this sheath and allow it to deploy. If this stent does not deploy to the full size, because the reaction forces of the artery wall and lesion site are too high, it must be further expanded by an additional post-dilatation procedure. Therefore, a separate post-dilatation catheter is needed, that has to be brought into the stented lesion site and then inflated to the full size. This is an extra, time-consuming step in the procedure.

BRIEF SUMMARY OF THE INVENTION

The present invention provides novel medical devices, such as vascular filters, with improved strength and flexibility and methods for their manufacture. These filters have a proximal frame section and a distal section, which can be collapsed into a small diameter delivery catheter and expanded upon release from this catheter. The proximal section is made as a frame of a relatively rigid material compared to the material of the distal section, for example a metal, and the distal section is provided with a flexible thin membrane, with perfusion holes in filter devices, of a diameter that allows blood to pass, but prevents the passage of emboli. The distal filter membrane has a proximal entrance mouth, which has almost the same size as the body lumen of a patient when the filter is deployed. The membrane is attached to the proximal section, which has the function to keep the mouth of the distal filter open and to prevent the passing of emboli between the body lumen wall and the edge of the filter mouth.

In order to have a good flexibility and a minimized crossing profile upon delivery, the membrane is made extremely thin. Tearing of the membrane is prevented by embedding in the filter membrane thin filaments of a material with high strength in the longitudinal direction, but high flexibility upon bending. Such a filter membrane with embedded filaments can have extreme flexibility and elasticity in certain directions, combined with limited deformation, high strength and prevention of crack propagation through the membrane material. Further, the filaments can be attached to the proximal frame section in such a way that the connection points act as hinges and as additional safety for the case that the membrane material might come loose from the frame.

The embedded filaments can include elements that help to give the membrane a desired shape after deployment.

The surface of the membrane filter may be coated with an additional material that improves the properties, for example the biocompatibility, drugs release or any other desired property, which the membrane itself does not offer.

The thus reinforced membranes can also be manufactured without holes for use for parts of catheters, inflatable parts, balloon pumps, replacement of body tissues, repair of body parts and functional parts like artificial valves and membranes, where minimal thickness and/or high strength are required.

Fibers are used not only as reinforcement for the membranes, but are also used as pulling fibers for the extraction the device from a delivery catheter or for retrieval, or retraction, of the device into a removal sheath. The frames can be used in temporary devices like a removable temporary stent, dilator, reamer, occlusion device for main artery or side artery, a housing for a graft, a valve, a delivery platform for drugs, radiation or gene therapy, or any other device that has to be placed and removed after some time. Applications are not restricted to arteries, but are meant for all body lumens.

Further, the invention provides a method for producing devices such as filters by dipping on a removable mold. According to this method, thin filaments of a material with high strength in the longitudinal direction, but high flexibility upon bending, are embedded in the filter membrane. The fibers are preferably less stretchable than the membrane material. The resulting composite membrane can have extreme flexibility and elasticity in certain directions, combined with limited deformation, high strength and prevention of crack propagation through the membrane material. Another function of the embedded filaments is that they help to give the membrane a desired shape after deployment.

The present invention also provides improved methods and devices that prevent escape of debris from the treatment site in a blood vessel, and more specifically prevent embolism, by installing at least one appropriate filter with millipores specific to its use downstream, and possibly one such filter downstream of the treatment site in a blood vessel and manipulating those filters in a manner to assure that any debris created at the treatment site or refluxing from closure of the filters will be removed from the vascular system by physical withdrawal of the filters and/or suction.

For example, an embodiment of the invention may be a multistage, for example two filter, system composed of a first filter to filter the blood flow and a second filter to entrap debris from the first filter.

The invention further relates to a catheter system for delivery of a self-expanding stent with a combined function of delivery from a central sheath and post-dilatation, the system including a catheter having an inflatable outer section that surrounds the sheath at the distal end section of the catheter. The first step in a procedure using this system is the release of the stent by pushing it out of the sheath and pulling back of the catheter over a distance that is equal to at least the length of the stent. Then the catheter is advanced once more until the inflatable section is lined up with the stent again. For post-dilatation the inflatable section is inflated and the lesion plus stent are further expanded.

In one embodiment of the invention, the central lumen within the delivery sheath, where the stent has been pushed out, is reinforced to prevent it from collapsing by the hydraulic pressure of the post-dilatation balloon that surrounds it. Reinforcement of this sheath can be provided by giving the catheter a suitable rigidity at its distal end, for example by giving the catheter an increased thickness at that end. This may make the delivery sheath too rigid, which can be a disadvantage for use in tortuous arteries.

Therefore, the invention makes use of a more flexible delivery sheath that is prevented from collapsing by the use of a separate reinforcement. A pre-dilatation balloon can be lined up with the delivery sheath and inflated until it fills the lumen of this delivery sheath. In this way a concentric arrangement of two balloons, separately inflatable, gives a strong post-dilatation device that is extremely flexible in the deflated state.

A single common guide wire is used to bring the catheters to the lesion site, and the pre-dilatation catheter acts as a guiding means for the stent delivery sheath/post-dilatation balloon. By removal of the pre-dilatation catheter, leaving the inflated delivery catheter in place, a proximal occlusion system is created with a large working channel (the delivery sheath). In combination with a distal occlusion means, e.g. a distal balloon, a closed chamber is created in the artery and this can be reached with a range of instruments for inspection, treatment and flushing/suction purposes.

BRIEF DESCRIPTION OF THE DRAWINGS

FIG. 17 shows a guide wire brought into an artery with a lesion.

FIG. 18 shows a guiding catheter with a distal protection means, brought across the lesion over the guide wire.

FIG. 19 shows how the distal protection means is deployed until it reaches the artery walls.

FIG. 20 shows a predilatation catheter, which has been advanced over the guiding catheter, in its predilatation position with inflated balloon in the lesion section. Further FIG. 20 shows a delivery sheath with an inflatable distal section, holding a compressed stent, which is advanced over the predilatation balloon catheter.

FIG. 21 shows how the predilatation balloon is deflated and advanced across the lesion site, plus the semi-deployed stent after it has been delivered in the lesion area.

In FIG. 22 the two balloons are lined up and brought in the stent.

In FIG. 23 the predilatation balloon is inflated to create a support for the inflatable delivery sheath.

In FIG. 24 the inflatable delivery sheath is inflated to perform the final angioplasty and to reach full deployment of the stent.

In FIG. 25 the predilatation balloon catheter is removed from the patient's body while the inflated sheath is still in place.

In FIG. 26 the chamber in the artery between distal protection means and inflated sheath is flushed to remove or catch all debris.

In FIG. 27 the sheath is deflated and the distal protection means is collapsed, thus enabling removal from the artery, leaving only the stent in place.

FIGS. 33–35 are side elevational views showing a third embodiment of a filter according to the present invention in three different stages of operation.

FIG. 35a is a detail view of a portion of the third embodiment in the operation stage of FIG. 35.

FIG. 35b is a detail view similar to that of FIG. 35a showing a modified version of a component of the embodiment of FIGS. 33–35.

FIGS. 36a and 36b are detail views of a modified form of construction of a portion of the embodiment of FIGS. 33–35.

FIG. 37 is a side elevational view showing a modified version of the third embodiment and includes an inset illustrating the modification to a larger scale.

FIG. 38 is a side elevational view showing the filter of FIG. 37 in a further possible operating stage.

FIG. 39 is a side elevational view showing a fourth embodiment of a filter according to the present invention.

DETAILED DESCRIPTION OF THE INVENTION

The invention provides a novel method and a system to confine and remove debris from a blood vessel, thereby preventing embolism in the vascular system.

A first step of one embodiment of a method according to the invention includes positioning a first particle filter in the blood vessel downstream of the treatment site.

Figure 1:
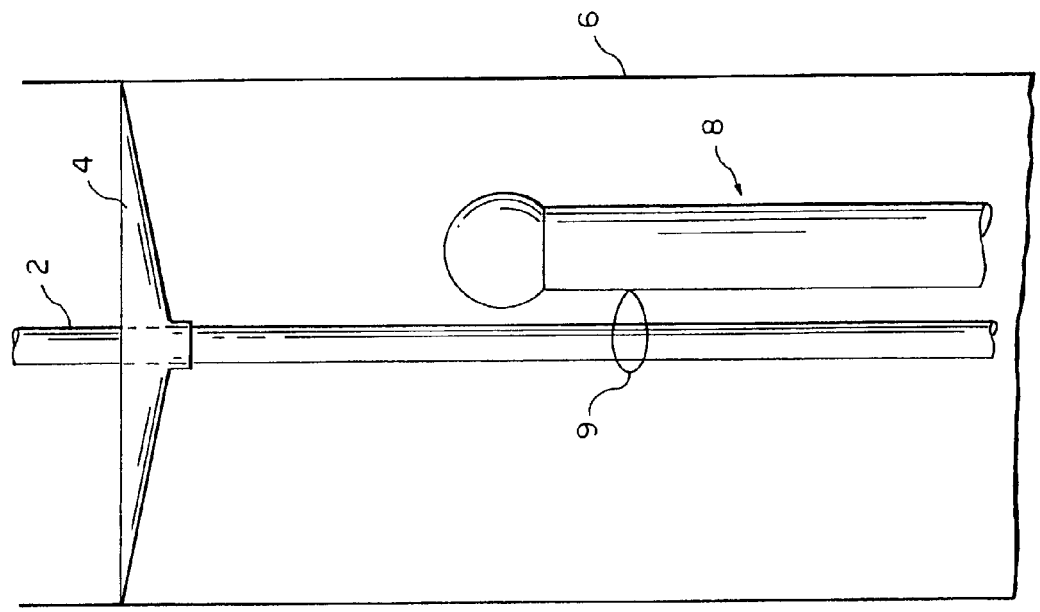
FIG. 1 is a simplified pictorial view illustrating a first component of a system according to the invention.

FIG. 1 is a cross-sectional elevational view of a first unit of a protective system according to the invention for carrying out the first step. This unit is composed of a sheath 1, a hollow guide wire 2 and a distal particle filter 4.

Filter 4 may have any shape, for example a conical shape, as shown, and is constructed to be radially expansible from a radially compressed state, shown in solid lines, to a radially expanded state, shown in broken lines at 4'. Preferably, at least one part of filter 4 is made of a resiliently deformable material that autonomously assumes the radially expanded state shown at 4' when unconstrained. Filter 4 may be shaped using appropriate shape setting procedures to open with a flared top portion made from highly elastic material such as the memory metal nitinol.

Sheath 1 serves to hold filter 4 in the radially compressed state during transport of filter 4 to and from the treatment site.

Filter 4 has a tip, or apex, that is fixed to guide wire 2. Guide wire 2 extends from a proximal end that will always be outside of the patient's body and accessible to the physician to a distal end that extends past the apex.

Guide wire 2 is preferably a hollow tube whose distal end is, according to the invention, used as a pressure sensor in communication with a pressure monitoring device 5 connected to the proximal end of guide wire 2. Device 5 is exposed to, and senses, via the longitudinal passage, or bore, in tube 2, the pressure adjacent to the distal end of guide wire 2.

Preferably, monitoring device 5 is removably fastened to the proximal end of guide wire 2. Device 5 would be removed, for example, when guide wire 2 is to be used to guide some other component of the device into the blood vessel after insertion of the first unit into a blood vessel, as will be described in greater detail below.

According to one practical embodiment of the invention, sheath 1 has an outside diameter of 1 to 1.5 mm and wire 2 has an outside diameter of 0.014–0.018 inch (approximately 0.5 mm) and is sized so that during insertion it will not disturb the obstruction that is to be removed. Filter 4 can be dimensioned to expand to an outer diameter of more than 1 mm, and preferably more than 10 mm. This dimension will be selected to be approximately as large as the diameter of the vessel to be treated.

Prior to insertion into a blood vessel filter 4 is arranged in sheath 1 as shown in FIG. 1. Then, in a conventional preliminary step, the blood vessel wall is punctured by a hollow needle, a preliminary guide wire (not shown) is introduced into the blood vessel through the needle, the needle is withdrawn, the opening in the blood vessel is dilated and a guiding catheter (not shown) is passed over the preliminary guide wire into the blood vessel to be treated. The distal, or leading, end of the guiding catheter is brought to an appropriate point ahead of an obstruction to be treated and the preliminary guide wire is withdrawn. Then, guide wire 2 and sheath 1, with filter 4 in place, are introduced into the blood vessel in the direction of blood flow, in a conventional manner through the guiding catheter, until filter 4 is at the desired location in the vessel, usually downstream of the obstruction to be treated. Introduction through the guiding catheter facilitates accurate passage of the filter 4 and sheath 1 by preventing buckling and permitting easier positioning, as well as reducing the risk of dislodging clot particles from the obstruction, which is typically plaque. Then, the operator holds wire 2 stationary and retracts sheath 1, which is long enough to be accessible to the operator outside the body, until sheath 1 moves clear of filter 4, which can then expand to take on the configuration shown at 4'. Sheath 1 can then be fully withdrawn from the vessel. Whenever required, the proximal end of sheath 1 can be clamped shut, usually during withdrawal.

Figure 2:
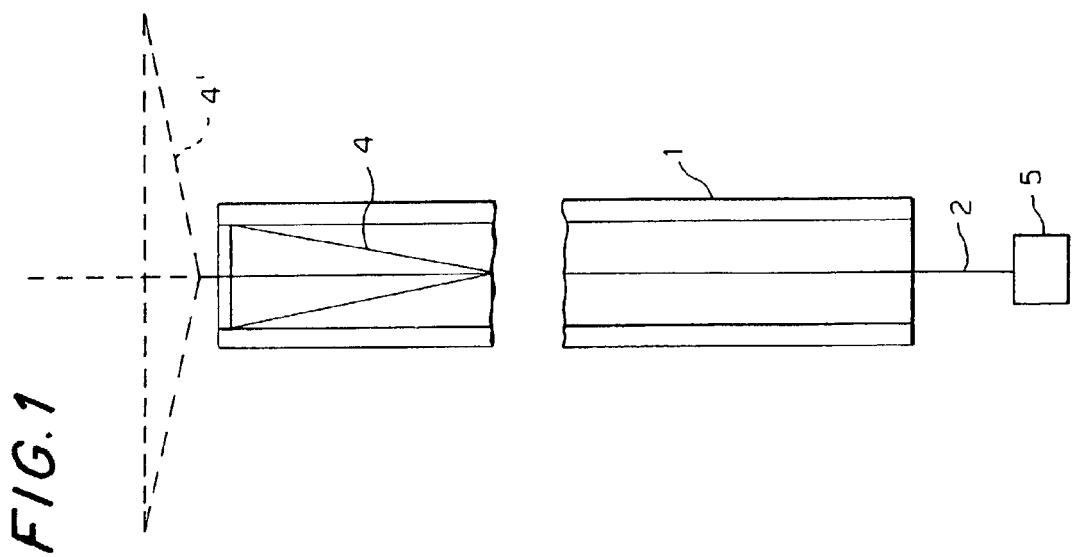
FIG. 2 is a simplified pictorial view showing the component for FIG. 1 in an expanded state, associated with a treatment device.

A second step of a method according to the invention involves performance of the desired medical treatment in the region upstream of filter 4, which region, as shown in FIG. 2, is below filter 4. Such a treatment can be for the purpose of removing an obstruction in a blood vessel 6, and this can involve any known angioplasty procedure or any known obstruction disintegration or observation (viewing) procedure employing ultrasound, laser radiation, stent placement, etc., or any mechanical cutting procedure, etc. The device for performing this function can be guided to the site by being advanced along guide wire 2.

For example, this device can be an ultrasonic device as disclosed in U.S. Pat. No. 4,870,953. This device has an output end 8 provided with a bulbous tip that applies ultrasonic vibrations to obstruction material, such as plaque or clot. Output end 8 may be guided to the site of the obstruction in any conventional manner over wire 2, however this can be assisted by providing output end 8 with a ring, or loop, 9 that is fitted around guide wire 2 before output end 8 is introduced into blood vessel 6.

After the device has been brought to the treatment site, it is operated to perform the desired treatment, in this case disintegration of plaque or clot, commonly predilation, stenting and stent dilatation. After the treatment has been performed, the treatment device is withdrawn from the blood vessel.

A third step of a method according to the invention includes positioning a second particle filter in the blood vessel upstream of first filter 4 and preferably upstream of the treatment site. This is accomplished by sliding guide wire 2 through an orifice in a second filter 14, to be described below, adjacent to a guide wire 12 that carries the second filter FIG. 3 is cross-sectional elevational view of a second unit of the protective system according to the invention for carrying out the third step.

This second unit is composed of a second tube, or sheath, 10, a second guide wire 12 and a proximal particle filter 14. Sheath 10 may have a diameter of the order of 3 mm. At the time this unit is inserted into the blood vessel, filter 4 remains in place in the blood vessel, in the expanded state as shown at 4' in FIG. 1, as does hollow guide wire 2.

Proximal filter 14 has an apex provided with a ring 16 through which guide wire 2 is inserted when the second unit is still located outside of the patient's body, in order to guide the second unit into the blood vessel up to the treatment site. Second guide wire 12 is secured to ring 16.

Figure 3:
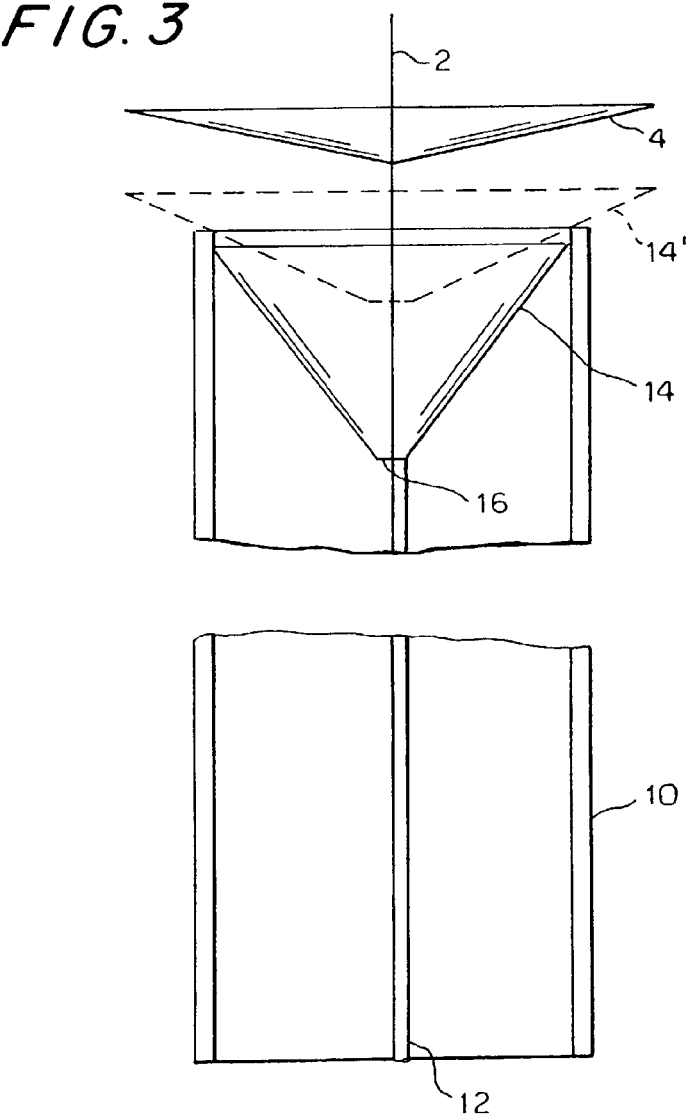
FIG. 3 is view similar to that of FIG. 1 showing the first component and a second component of a system according to the invention.

Prior to introduction into the patient's body, filter 14 is installed in sheath 10 in the manner illustrated in FIG. 3. The second unit is then placed over guide wire 2 and advanced into the blood vessel to the desired location.

After the second unit has been brought to the desired location, proximal filter 14 is held stationary by holding stationary the end of guide wire 12 that is outside of the patient's body, while retracting sheath 10. When filter 14 is clear of the distal end of sheath 10, filter 14 expands radially into the configuration shown at 14' to engage filter 4. This step is completed when filter 14 is fully radially expanded.

Because of the porous nature of filters 4 and 14, a reasonable volume of blood flow can be maintained in the blood vessel when the filters are deployed.

Prior to introduction of filter 14, any debris produced by the treatment performed in the second step will be conveyed by blood flowing to and through radially expanded filter 4, where the debris will tend to remain. During and after introduction of filter 14 and expansion of filter 14 into the configuration shown at 14', suction may be applied to the region between the filters through sheath 10. This will help to assure that the debris remains trapped between the two filters.

Then, in a fourth step, debris is removed from blood vessel 6 by pulling wire 2 to move filter 4 toward, and into contact with, filter 14, then retracting both filters into sheath 10 by pulling the guide wires 2 and 12, thus withdrawing the assembly of filters 4 and 14 into sheath 10. Sheath 10 with enclosed filters is then withdrawn through the guiding catheter (not shown), which is subsequently removed from the blood vessel using standard procedures. These operations are performed by pulling on guide wire 2 at its proximal end, located outside of the patient's body, while initially holding guide wire 12 stationary until filter 4, comes to nest within filter 14. Then both guide wires 2 and 12 are pulled in order to retract the filters into sheath 10. Finally, both of the guide wires and sheath 10 are pulled as a unit out of the blood vessel. During any portion, or the entirety, of this step, suction may continue to be applied to filters 4 and 14 through sheath 10.

Figure 4A:
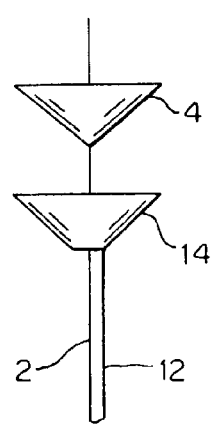
FIGS. 4A and 4B are simplified pictorial views showing two basic embodiments of the invention.
Figure 4B:
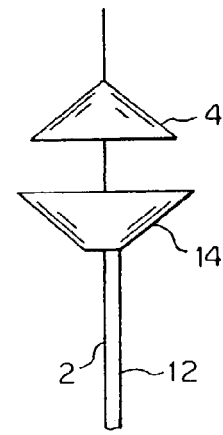

FIGS. 4A and 4B are simplified pictorial views showing two possible arrangements for a set of filters 4 and 14. The arrangement shown in FIG. 4A corresponds to that shown in FIGS. 1, 2 and 3. The arrangement shown in FIG. 4B differs in that filter 4 is inverted relative to the orientation shown in FIGS. 1, 2, 3 and 4A. The arrangement of filters shown in FIG. 4A is applicable to short, non tortuous segments of arteries. FIG. 4B shows an optional filter arrangement for longer segments of arteries especially if they are tortuous.

When the arrangement shown in FIG. 4B is employed, filters 4 and 14 are positioned in the blood vessel by the first and third steps as described above. In order to withdraw the filters, guide wire 2 is pulled to bring filter 4 into a position in which its large diameter end has been introduced into the large diameter end of filter 14. Then, as both filters are pulled into sheath 10, filter 14 is collapsed by its contact with sheath 10 and filter 4 is collapsed by its contact with the interior of filter 14. In this form of construction, filter 14 has an expanded diameter at least slightly greater than filter 4.

The arrangement illustrated in FIG. 4B offers the advantages that in the first step filter 4 can be extracted from sheath 1 somewhat more easily and, after filter 4 has been expanded, any debris produced by the operation performed in the second step will tend to collect near the apex of filter 4, away from its line of contact with the blood vessel wall.

Figure 5:
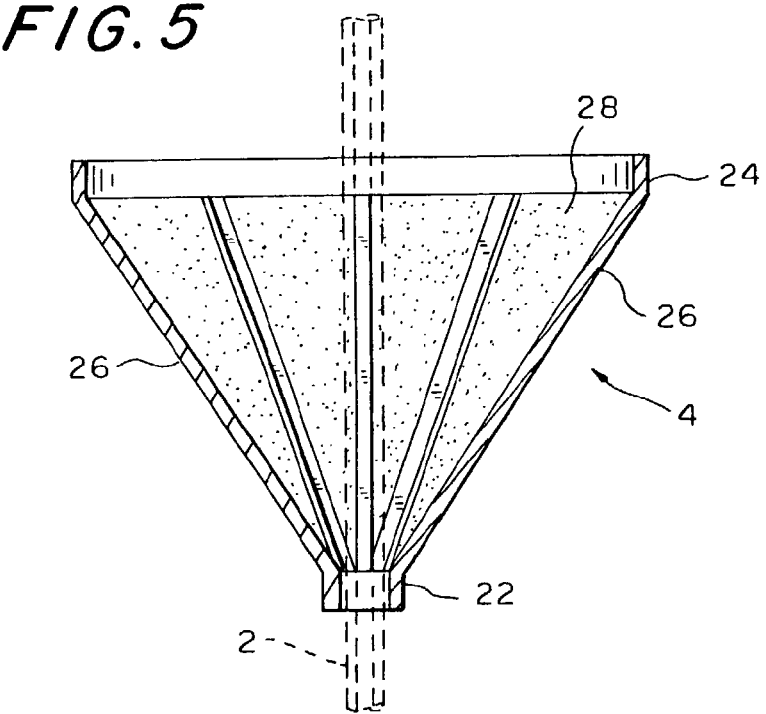
FIGS. 5, 6 and 7A are cross-sectional elevational views of various alternative embodiments of filter components of a system according to the invention.

One exemplary embodiment of filter 4 is shown in greater detail in FIG. 5. This embodiment consist of a frame, or armature, composed of a small diameter ring 22 at the apex of filter 4, a large diameter ring 24 at the large diameter end of filter 4 and a plurality of struts 26 extending between rings 22 and 24. The frame is preferably made in one piece of a relatively thin memory metal, which is well known in the art. One example of such a metal is nitinol. The frame is constructed to normally assume a radially expanded state, such as shown at 4' in FIG. 1, but to be easily deformed so as to be retracted, or radially compressed, into sheath 1.

The frame is covered on its outer surface with a thin sheet, or membrane, 28 of suitable filter material having pores that are sized according to principles known in the art to protect organs downstream of the treatment site. The pore dimensions are selected to allow reasonable flow of blood to organs downstream of the treatment site when the filters are in place while trapping debris particles of a size capable of causing injury to such organs. The desired filtering action will be achieved with pore sized in the range of 50 μm to 300 μm. This allows different millipore sizes to be used to optimize either blood flow or embolism protection. The larger pore dimensions will be used in situations where a higher blood flow rate must be maintained and the escape of small debris particles is medically acceptable.

Figure 6:
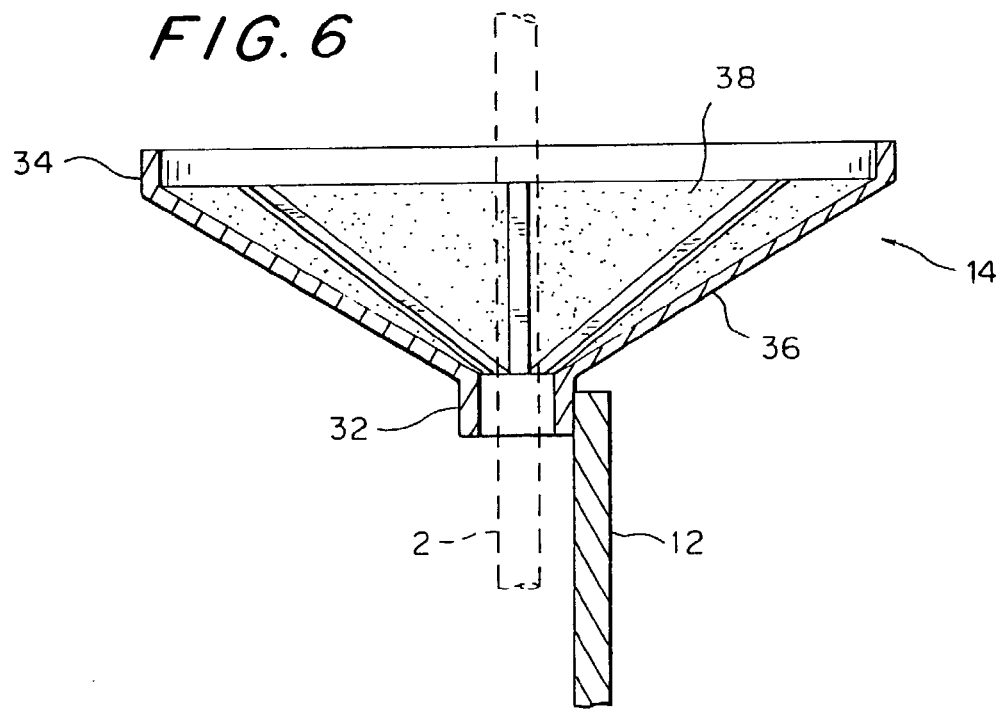

FIG. 6 is a view similar to that of FIG. 5 showing one suitable embodiment of filter 14, which is here shown essentially in its expanded state. Like filter 4, filter 14 includes a frame, or armature, having a small diameter ring 32 at its apex, a large diameter ring 34 at its large diameter end and a plurality of struts extending between rings 32 and 34. Filter 14 is completed by a filter sheet, or membrane, 38 secured to the outer surfaces of struts 36. Ring 32 provides a passage for guide wire 2, the passage being dimensioned to allow filter 14 to move freely along guide wire 2. Guide wire 12 is fixed to the outer surface of ring 32.

Figure 7A:
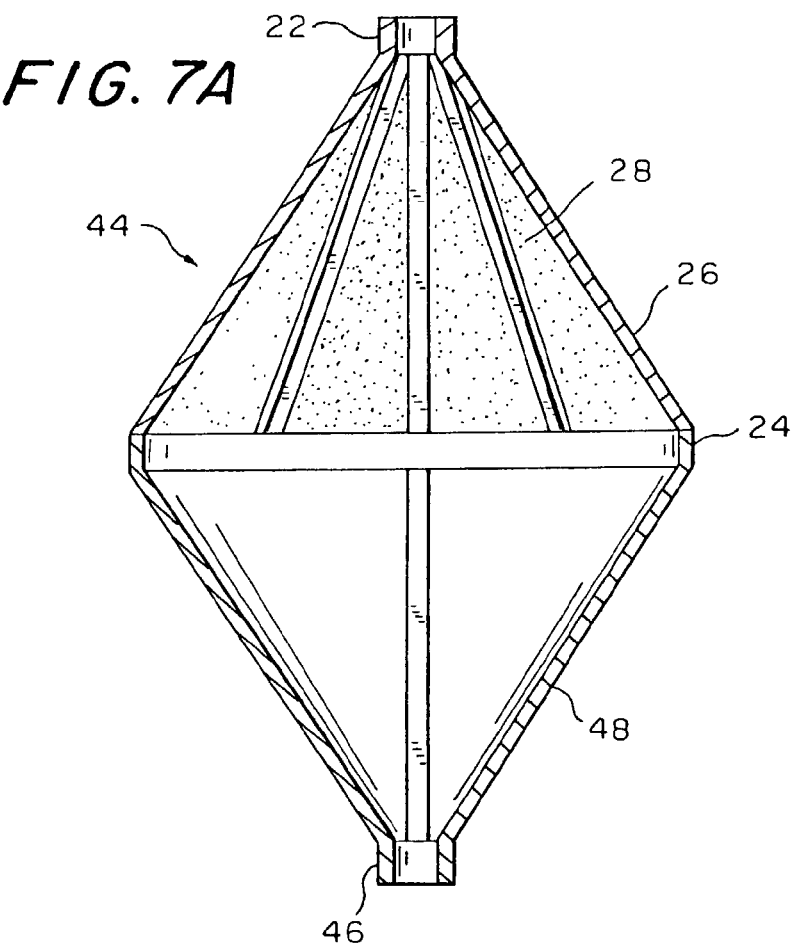
Figure 7B:
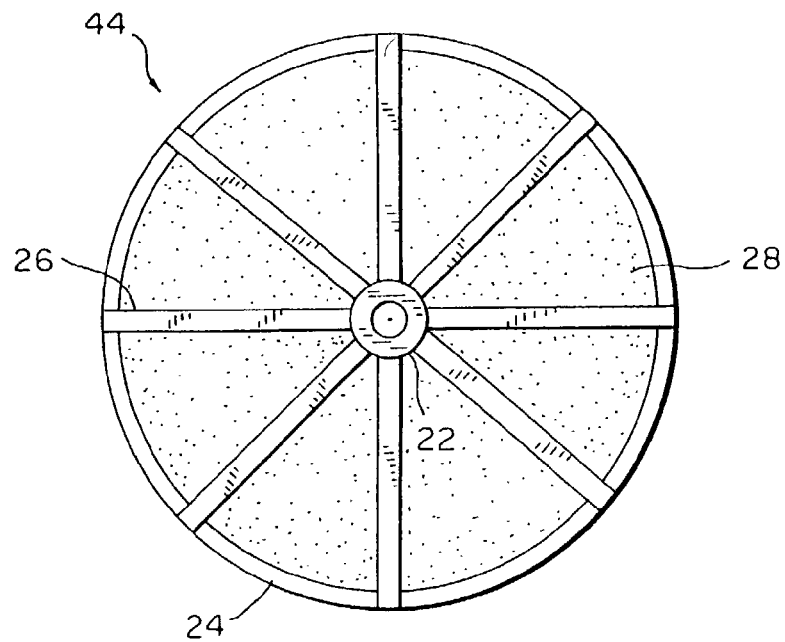
FIG. 7B is plan view of the embodiment shown in FIG. 7A.

FIGS. 7A and 7B are, respectively, an elevational cross-sectional view and a plan view of another embodiment of a distal filter 44 that can be employed in place of filter 4. This embodiment includes, like filter 4, a small diameter ring 22, a large diameter ring 24 and a plurality of struts 26, with a filter sheet 28 secured to the outer surfaces of struts 26. Here again, ring 22 has an opening for receiving guide wire 2, which will be fixed to ring 22.

Filter 44 is further provided with a second, small diameter, ring 46 and a second series of struts 48 extending between rings 24 and 46. Ring 46 has an opening with a diameter larger then that of guide wire 2, so that ring 46 is moveable relative to guide wire 2.

All the parts of filter 44, except for membrane 28, like the corresponding parts of filter 4 and 14, may be made in one piece of a memory metal that has been processed to bias the filter toward its radially expanded configuration. All of these components are sufficiently thin to allow the filter to be easily collapsed radially within its respective sheath 1 or 10. Filter 44 will be mounted so that its apex faces in the distal direction, i.e. the cone formed by the struts 26 and filter sheet 28 have an orientation which is opposite to that of filter 4.

Filter 44 is brought to its radially expanded state in essentially the same manner as filter 4. When the filter portion is at the desired location in the blood vessel, sheath 1 will be retracted in order to allow filter 44 to expand radially. When the filters are to be withdrawn, guide wire 2 is pulled in the proximal direction until the lower part of filter 44, composed of ring 46 and strut 48, comes to nest either partially or fully in filter 14. Then, both guide wires 2 and 12 can be pulled in the proximal direction in order to retract the filters into sheath 10. During this operation, ring 46 has a certain freedom of movement relative to guide wire 2, which will help to facilitate the radial contraction of filter 44. Alternatively, or in addition, sheath 10 can be advanced in the distal direction to assist the retraction operation.

According to further alternatives, rings 22 and 46 can be dimensioned so that either guide wire 2 is fastened to ring 46 and movable longitudinally relative to ring 22, or guide wire 2 is fixed to both rings 22 and 46. In the latter case, radial contraction and expansion of filter 44 will still be possible in view of the flexibility and deformability of its components.

Figure 8:
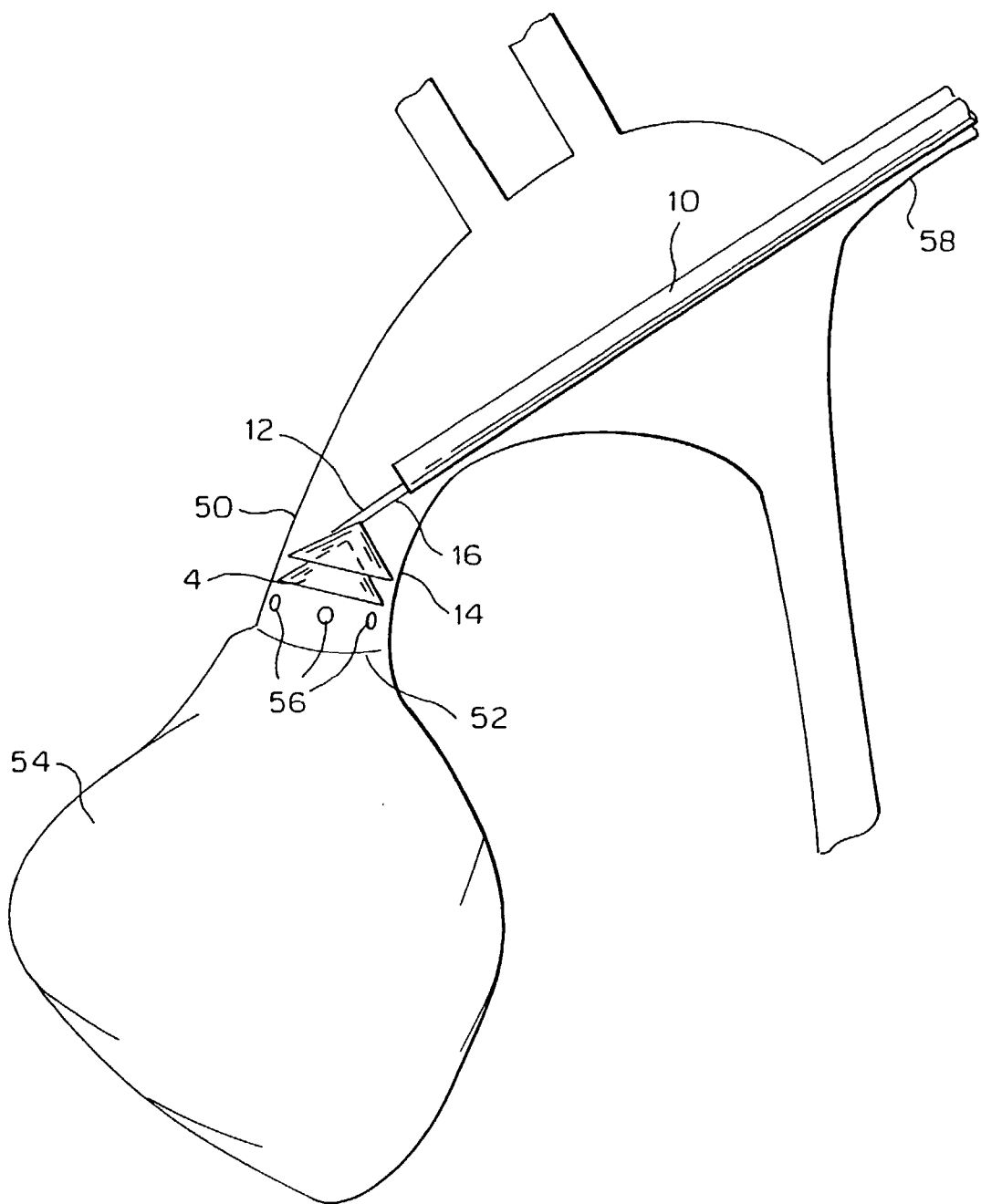
FIGS. 8, 9 and 10 are simplified pictorial views illustrating specific procedures that may be carried out with a system according to the invention.

A system according to the invention can be used, for example, to improve the safety of bypass surgery. Referring to FIG. 8, an example of that surgery involves attaching vein bypass grafts to the aorta 50 starting from a point just downstream of the aortic valve 52 located between the left ventricle and aorta of the heart 54. In such a procedure, holes 56 are cut in aorta 50 for insertion of the upstream ends of the grafts. The operation of cutting into the watl of the aorta to sew on grafts can produce debris that will be carried along with blood flowing through the aorta to locations in the circulatory system where it can create an embolism in various organs, including the brain.

Referring to FIG. 8, the risk of such an occurrence can be reduced by introducing a system according to the embodiment of FIGS. 1–3, before holes 56 are cut, through a subclavian artery 58, which can be accessed via the patient's arm, and the brachial artery, to bring filters 4 and 14 to a location downstream of the location where holes 56 will be cut and to expand those filters so that they extend across the blood flow path through the aorta. Then, when holes 56 are cut, any debris produced by the cutting operation will be trapped, at least initially, within filter 4. However, while both filters are being withdrawn into tube 10, after holes 56 have been cut and possibly after vein grafts have been sutured to the holes, some debris may be squeezed out of filter 4, even as suction is being applied through tube 10. If this should occur, the debris can be drawn into filter 14 so as to be safely removed from the circulatory system.

Figure 9:
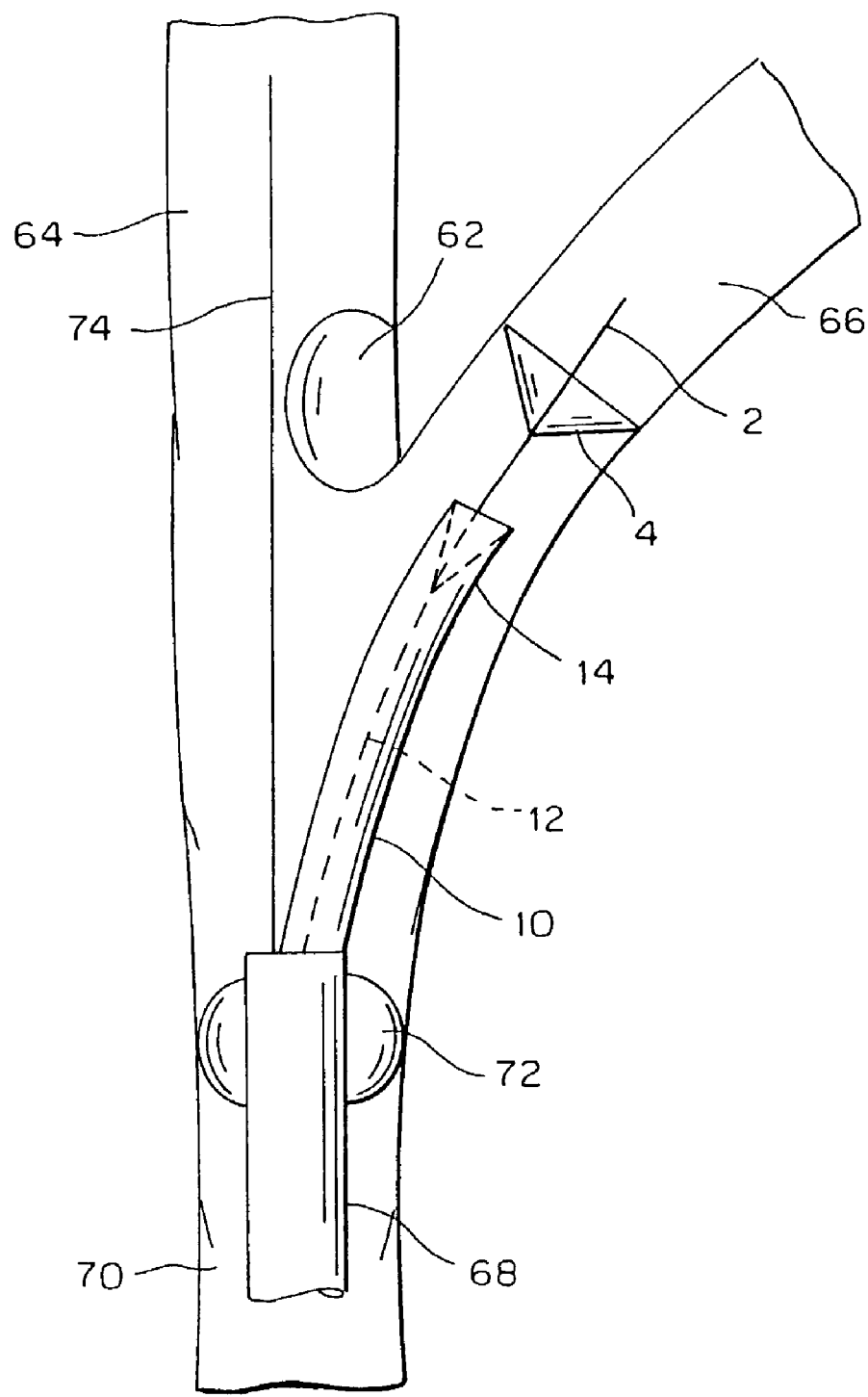

Another example of the use of a system according to the invention to capture debris incident to a medical procedure is illustrated in FIG. 9. A plaque deposit 62 is present on the wall of an internal carotid artery 64 just downstream of the junction with an associated external carotid artery 66. A guiding catheter 68 is introduced into common carotid artery 70 and is used as a conduit for introducing all other devices required to removes plaque 62 and collect the resulting debris. Catheter 68 carries an annular blocking balloon 72 on its outer surface and is provided with a conduit (not shown) for supplying inflation fluid to balloon 72.

A wire 74 carrying a Doppler flow sensor is introduced into internal artery 64 to position the flow sensor downstream of plaque 62. Then, sheath 1 (not shown) is introduced to deploy filter 4 in external artery 66, as described earlier herein and balloon 72 is inflated to block blood flow around catheter 68. After filter 4 is deployed and balloon 72 is inflated, any conventional procedure, such as described above with reference to FIG. 2, can be carried out to disintegrate plaque 62.

Then, as described with reference to FIG. 3, sheath 12 is advanced through catheter 68 to the location shown in FIG. 9, filter 14 is deployed and expanded into internal artery 66, and suction is applied as filters 4 and 14 are retracted into sheath 10.

In this procedure, starting from a time before disintegration of plaque 62, blood flow through common carotid artery 70 is blocked by inflated balloon 72. This results in a retrograde flow in internal artery 64 back toward common artery 70 and then antigrade flow into external artery 66, where debris being carried by the blood flow will be trapped on filter 4. The pressure sensing wire 74 is used to ascertain the collateral pressure, which must always exceed 40 mm Hg in the carotid. After a sufficient period of time has elapsed, filter 14 will be deployed to nest against filter 4 and both filters will be retracted into sheath 10 while suction is applied, possibly through sheath 10. Then, balloon 72 will be deflated, sheath 10 will be withdrawn through guide catheter 68 and catheter 68 will be withdrawn.

In another application of the invention, the filters can be passed through a small peripheral artery into the aortic root to entrap debris generated during cardiac surgery. Such a device can be used during surgery or can be implanted for long-term use to prevent migration of blood clots to the brain under certain circumstances, such as during atrial fibrillation.

Figure 10:
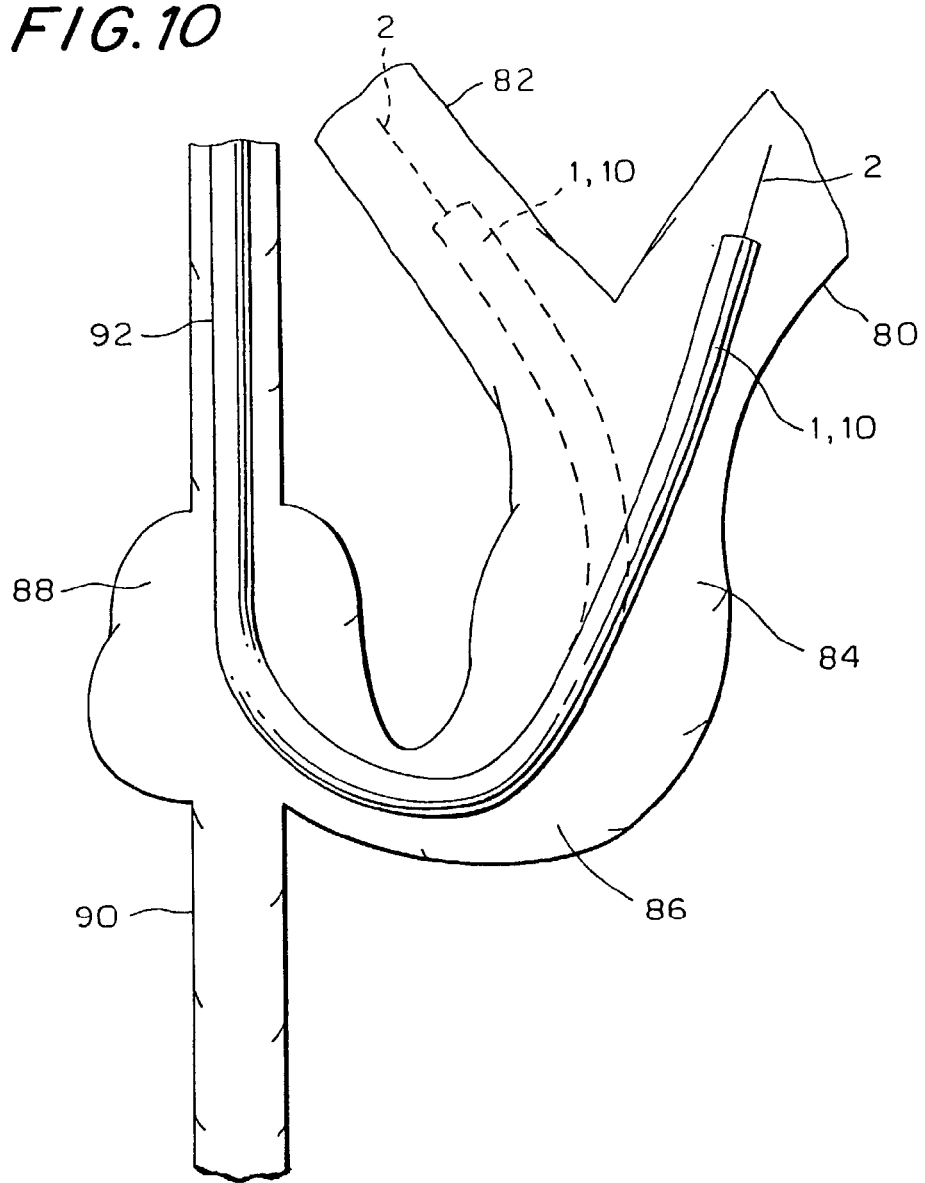

A further example of procedures that may be carried out with a device according to the invention is illustrated in FIG. 10, which shows the positioning of a device according the invention for treating an obstruction in an artery 80 or 82 emerging from the pulmonary artery 84 connected to the right ventricle 86 of a patient's heart. The right ventricle communicates with the right auricle 88 of the heart, which is supplied with blood from veins 90 and 92. In such a procedure, sheaths 1 and 10 may be introduced through either vein 90 or 92 and then through auricle 88, ventricle 86 and pulmonary artery 84 into either one of arteries 80 and 82 to be treated. Techniques for guiding the sheaths along the path illustrated are already well known in the art. Once positioned in the appropriate artery 80 or 82, an obstruction removal procedure will be performed in the manner described above.

Figure 11:
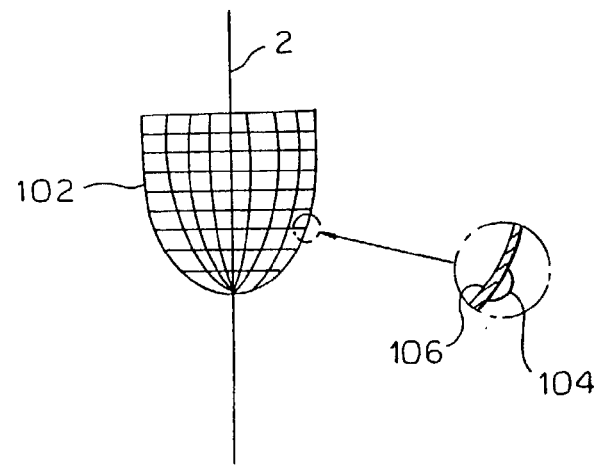
FIG. 11 is an elevational view of another embodiment of a filter component of a system according to the invention.

FIG. 11 shows another embodiment of a filter component according to the invention in the general form of a basket, or cup, 102 made of a layer 104 of a radially compressible, autonomously expandable, material, such as a memory metal, and a filter sheet 106. Layer 104 may be fabricated by weaving memory metal wire into a mesh, or screen. Filter sheet 106 is made of a suitable plastic material, such as polyester, perforated to provide the desired filter pores, having dimensions described above. The bottom of basket 102 may be fixed to guide wire 2, in the manner of filter 4, described above, or may have a circular opening that is slidable along wire 2, with a second guide wire attached to the edge of the opening, in the manner of filter 14, as described above. Each such basket 102 will be used in the same manner as a respective one of filters 4 and 14 and will be dimensioned to extend across the blood vessel at the location where the system is to be employed.

The procedures described above are merely exemplary of many procedures that can be aided by utilization of the system according to the present invention and other uses will be readily apparent to medical professionals. It should further be clear that the examples shown in the drawings are illustrated in a schematic form. For example the shape of the ring 24 in FIGS. 5, 7A and 7B is shown as a circle. However, for a ring that has to be collapsed to allow the filter to be pulled it into the sheath, it would be more logical to give it a slightly wavy or corrugated shape. This would make it more flexible and capable of smooth radial contraction and expansion. Another embodiment of a system having a distal protection system with a double filter according to the invention is shown in FIGS. 12–16.

Figure 12:
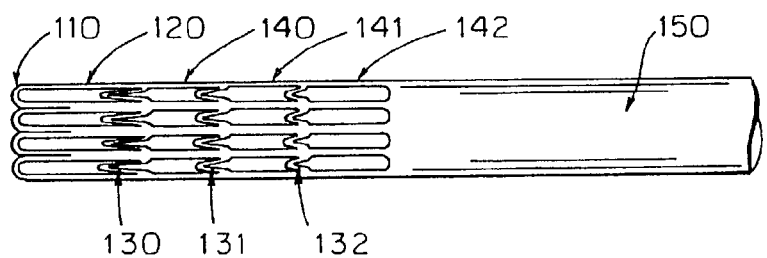
FIG. 12 is a side elevational view of a component of another embodiment of a system according to the invention, including a filter in its folded state.
Figure 13:
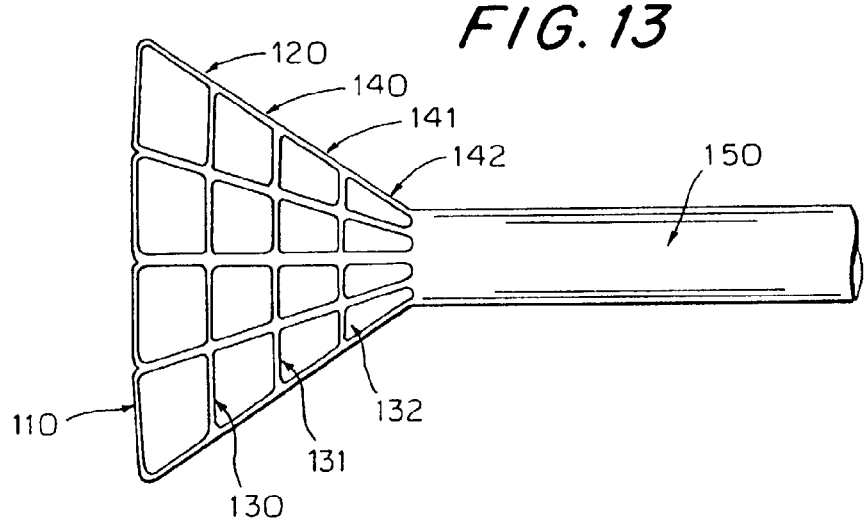
FIG. 13 is a view similar to that of FIG. 12, showing the filter in its expanded sate.
Figure 14:
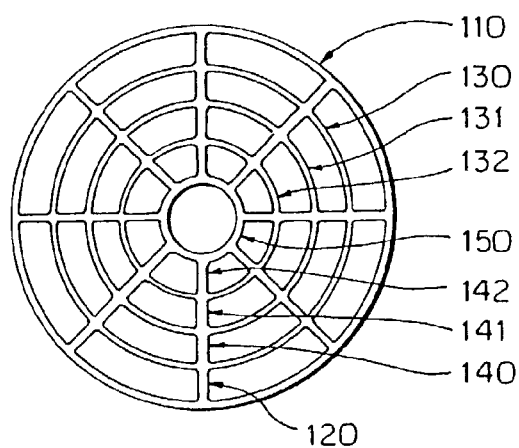
FIG. 14 is an end view of the component with the filter in the expanded state.

In FIG. 12–14, a circularly cylindrical tube 150 is formed to have, at one end, which is here its distal end, a monolithic, or one-piece, distal filter that has a tubular conical shape with a pattern of slots that have been made in the surface of tube 150 by cutting, grinding, etching or any other technique. Tube 150 can be made of any material, like metal or polymer, and especially of nitinol with superelastic properties. Tube 150 may be long enough to be used as a guiding rail for catheters that are used for the angioplasty/stenting procedure.

At the distal end of tube 150, the slots are cut in such a way as to form a filter that has an expansion capability of at least, for example, a factor of 4. If tube 150 is made of nitinol, the expanded shape can be programmed into the memory by a heat treatment, while the material is kept in the desired expanded shape, shown in FIGS. 13 and 14, by some restraining tool. This is a known technique called shape setting.

The slots cut at the distal end of tube 150 leave thin, circularly curved, circumferential groups of distal strips 110 and groups of intermediate strips 130, 131 and 132. These strips are connected to, and interconnected by, thicker longitudinally and radially extending groups of struts 120, 140, 141 and 142 that end at the continuous, i.e., imperforate, surface of tube 150. Upon expansion for shape setting, struts 120, 140, 141 and 142 will bend out and give the distal section of tube 150 a conical shape. The thinner strips 110, 130, 131 and 132 will deform to follow circular arcuate paths during shape setting.

Tube 150 may have a length sufficient to have its proximal end (not shown) extend out of the patient's body where the surgeon can manipulate it. Tube 150 can also be shorter and attached to a separate guide wire to save costs or to reduce the diameter over the majority of the length.

The geometry of the strips and struts is chosen so that deformation upon shape setting and during expansion/contraction stays below acceptable limits. If necessary the cutting pattern of the strips can include some solid hinges. These are preferential bending spots, created by locally reduced thickness of the material. In this way it is also possible to cause a proper folding up of the strips while the filter is forced back into the cylindrical shape after conical shape setting.

In FIG. 12 the filter at the distal end of tube 150 is shown in its folded, or radially compressed, state, as it would appear when installed in sheath 1 of FIG. 1. FIGS. 13 and 14 show the final shape of the filter after shape setting and then after deployment from sheath 1. Distal strips 110 create a non-traumatic rim with a smooth series of tangential connections between the struts 120. The series of strips 130, 131 and 132 connect the long struts 120, 140, 141, and 142 together at different intermediate positions, but in principle intermediate strips 130, 131 and 132 could be omitted, at least if there are a sufficient number of longitudinal struts 120, 140–142 to create the desired fine mesh. However, the feasible number of struts is limited by the following parameters:

The initial tube diameter;
The minimum width of each slot, determined by the tooling;
The minimum required width for a stable strut; and The desired expansion ratio determined by the acceptable length of each strut.

If the filter pores, constituted by the slots, are not fine enough, because the open area between the struts of an expanded filter becomes too large, additional circumferential groups of strips can be provided to make the mesh finer. The number of strips can be chosen freely, because they do not have an influence on the expansion ratio. For clarity only four rows of strips are shown in FIGS. 12–14. As can be seen, the length of the strips changes from proximal to distal. For example, strips 130 are longer than strips 131 and 132.

FIG. 14 shows a top view of the expanded filter where the strips 110 have been shape set to create a smooth rim that can perfectly cover the whole cross section of an artery with a good fit.

The conical filter shown in FIGS. 12–14 is meant to be used in combination with a delivery sheath, as described herein with reference to FIG. 1. Such a sheath can run over the surface of tube 150 and if the sheath is retracted, the filter will assume the conical shape shown in FIGS. 13 and 14, which is substantially the same as the shaping pattern of FIG. 1. When such a delivery sheath, surrounding a collapsed filter, is brought into an artery and then gently withdrawn, the filter will open up, flare out and completely obstruct the cross section of the artery. Nitinol is an excellent material for such a filter, because it can withstand high elastic strains. A nitinol filter according to this design can be deployed and collapsed elastically several times without any plastic deformation, whereas known filter materials would fail.

Figure 15:
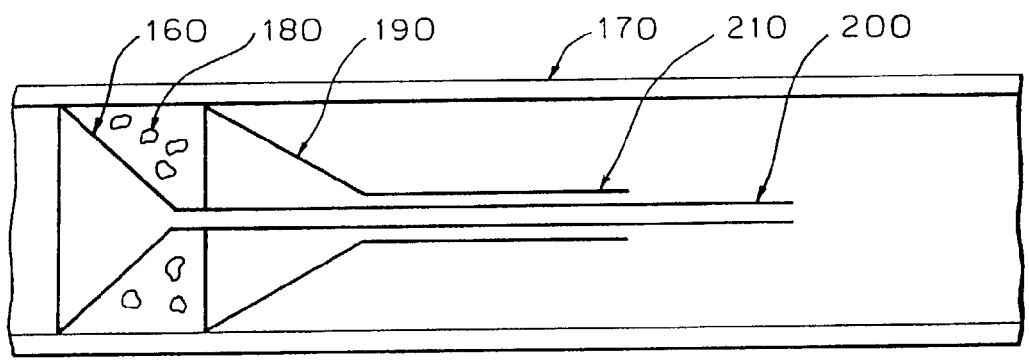
FIG. 15 is a simplified side cross-sectional view showing the other embodiment of a system in a blood vessel with two filters of the type shown in FIGS. 12–14.

In FIG. 15 a pair of filters 160 and 190 each having the form shown in FIGS. 12–14 according to the invention are used in combination in order to entrap emboli particles between them for removal from the artery.

During the major part of an angioplasty/stenting procedure, only the most distal filter 160 is in place. During angioplasty/stenting of the artery 170, emboli particles 180 may be released from the lesion site and move with the blood stream until they are stopped by filter 160. At the end of the procedure, a second filter 190 is advanced over the wire or tube 200 that is connected to filter 160. The diameters of the distal ends of filters 160 and 190 are about the same, and filter 190 can completely be advanced over filter 160, when it is delivered from its own delivery sheath (not shown). Filter 190 has its own tube 210, which has a much larger inner diameter than the outer diameter of wire or tube 200 of the first filter 160. The lumen between both tubes 200 and 210 can be used for flushing/suction. Of course this can also be performed through tube 200 as well.

Figure 16:
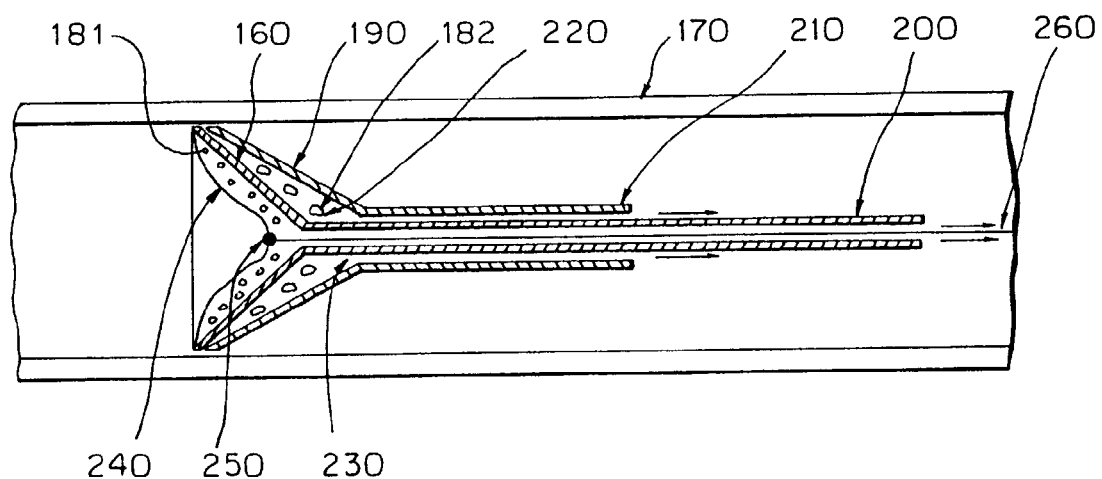
FIG. 16 is a view similar to that of FIG. 15 showing a modified form of construction of the system shown in FIG. 15.

FIG. 16 shows the system of FIG. 15, with the thickness dimensions of the various components illustrated more clearly, at a point in a procedure just after the second filter 190 has been brought into a position to enclose the first filter 160, with the distal ends of both filters in contact with one another. The opening angles of both filters may be identical or, as shown, different. In case they are identical, the surfaces of both filters will mate perfectly and all debris will be trapped, like in a sandwich, between the two conical surfaces.

However, if the cone of the second filter 190 has a smaller opening angle than filter 160, as shown, the situation shown in FIG. 16 will result. The distal edges of both filters fit well together, but for the rest there is a gap between the surfaces of the two filters. This gap creates a chamber 220, in which small particles can freely move. The advantage of this arrangement is that the particles can be removed from chamber 220 by suction through the lumen 230 between tubes 200 and 210.

FIG. 16 further shows an additional filter sheet 240 that is used to capture fine particles that go through the holes in filter 160. The holes in the filter 160 can for example have a maximum size of 250 µm, while filter sheet 240 can be provided with holes, or pores, having a size of the order of only 150 µm or less, dependant on the application.

Filter sheet 240 may be made of a fine metal sheet, a polymer, or any other flexible tissue and it can be attached to the distal strips 110 of filter 160 by means of glue, stitching or any other means. At its proximal extremity, corresponding to its center, sheet 240 may a central connection point 250 that is connected to a long wire 260 that runs completely through tube 200 to a location outside of the patient's body. With this wire 260, filter sheet 240 can be pulled into a conical configuration before filter 160 is pulled into its delivery sheath (not shown). This makes it easier to bring filter 160 and filter 240 into a smooth collapsed state. Once filter 160 is deployed, or expanded, wire 260 may be released a little bit to enable filter sheet 240 to move away from filter 160, thus creating additional space for entrapment of the small particles 181 that fit through the holes in filter 160. The larger particles 182 will not go through filter 160 and will stay at the proximal side of this filter. If chamber 220 between the conical surfaces of filters 160 and 190 is large enough, and if wire 260 of filter sheet 240 is not pulled too tight, most particles can easily be suctioned out through lumen 230. By pulling wire 260, the particles 181 will be forced to move in the direction of the suction opening. This is another advantage of the use of a movable filter sheet 240.

Finally only some very large particles will remain in chamber 220, and they can be removed by holding them entrapped between the surfaces of the filters, while both filters are pulled back into the delivery sheath and the filters are compressed, or collapsed to their cylindrical configurations. This is done while continuous suction is applied.

In case the large particles are squeezed, break up and slide through the holes in filter 160, they will again be gathered in filter sheet 240. Eventually wire 260 can be released even more if there is a lot of material between filter 160 and filter sheet 240. In that case, filter sheet 240 may look like a bag, filled with material, that hangs on the distal side of the completely collapsed filter 160. This bag may not be pulled back into the delivery sheath, but will just be pulled out of the artery while it hangs at the distal tip of the sheath.

A major advantage of this double filter design is that upon compression of the filter cones, the emboli particles can only leave the chamber 220 through the suction lumen 230, or they stay there to be finally entrapped mechanically between the cone surfaces or to remain in the bag.

The distal filter will be in place during the whole procedure of angioplasty/stenting and therefore the mesh size is very important. An additional pressure-measuring tip, distally in the blood stream may monitor perfusion. The wire that holds this tip may be integrated with wire 260 that is controlling the filter sheet 240. Alternatively, wire 260 can have the form of guide wire 2 shown in FIG. 1, with a lumen connected to a pressure detector.

On the other hand, filter 190 is only used a very short time and therefore its mesh size may even be finer than that of filter 160.

As explained above, the number of longitudinal struts is limited on the basis of the desired expansion ratio. The distance between two circumferential strips can be made rather small, but they must still be able to be bent in order to get a collapsable and expandable device. Therefore a certain gap must remain between them. Normally such a gap would be larger that 50 µm, so an additional filter mesh is required in case the allowed particle size is 50 µm, such as for use as a filter in a carotid artery.

In general, filter systems according to the invention can have many embodiments, including systems containing a distal filter with or without an additional filter mesh with a proximal filter, also with or without an additional filter sheet. Also the relative position of filter and filter sheet can be varied. The sheet can be outside of filter 160. Further embodiments can be combinations of emboli catching devices of different geometries and/or types. Filters, balloons and sponges of all kinds can be used in multiple combinations, all based upon the principle of full entrapment of particles before the protection device is collapsed upon removal from the patient's body. Combinations of an inflatable delivery sheath according to the invention with a multi-filter arrangement, as disclosed, are also meant to be an embodiment of this invention.

FIGS. 17–27 illustrate the structure and successive phases in the use of another embodiment of the invention that is suitable for performing angioplasty procedures while trapping and removing debris produced by the procedures.

Figure 17:
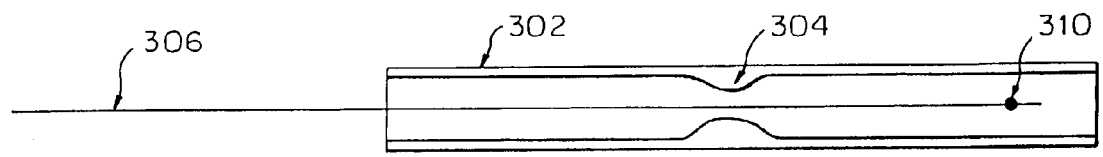
FIGS. 17–27 are simplified pictorial views showing successive stages in an angioplasty and stenting procedure using an embodiment of a system according to the invention.

FIG. 17 shows an artery 302 with an obstruction, or lesion site, 304 that reduces the effective diameter of artery 302. The invention can be used to treat virtually any artery throughout the body, such as for example the inner carotid artery where emboli are extremely dangerous because the particles can cause stroke in the brain.

A first component of this embodiment is a guide wire 306 that, in a first step of a procedure using this embodiment, is advanced through artery 302, normally in the direction of blood flow, and past lesion site 304. The blood pressure in artery 302 adjacent the distal end of guide wire 306 can be monitored by a pressure monitoring device that includes a miniature pressure sensor, or transducer, 310 at the distal end of guide wire 306 and a signal measuring unit at the proximal end, as represented by element 5 in FIG. 1. Guide wire 306 can be provided with a longitudinal lumen that can contain wires or an optical fiber to transmit electrical or optical signals from sensor 310 to the signal measuring unit and the signal measuring unit can be connected to a conventional indicator, display and/or warning device. Sensor 310 may be, for example, a distal miniature load cell, possibly of the type having a load-dependent electrical resistance. The pressure monitoring device can continuously monitor the blood pressure in artery 302 during an entire procedure.

Figure 18:
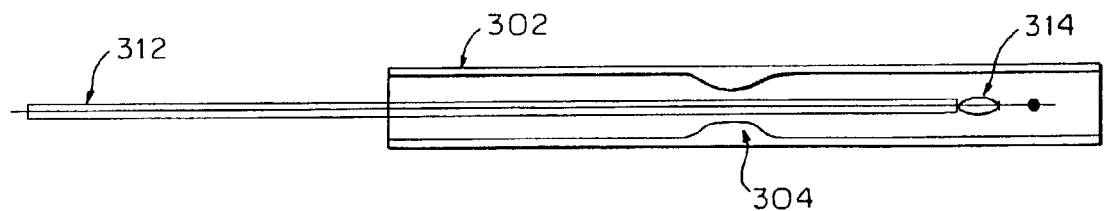

FIG. 18 shows the second step in which a guiding catheter, or sheath, 312 having a longitudinal lumen carrying a distal protection means 314 is advanced over guide wire 306 until means 314 reaches a location that is distal, or downstream, of lesion site 304. If distal protection means 314 is a filter made from a small slotted nitinol tube, it can be advanced over guide wire 306 while being retained in the lumen that extends through catheter 312.

Distal protection means 314 may be a filter, as described earlier herein, or a blocking balloon, or possibly a compressible sponge element. For example, means 314 may be an expandable filter cone, or umbrella, having the form disclosed, and deployed and retracted in the manner disclosed, earlier herein with reference to FIGS. 1–14, and particularly FIGS. 12–14, held in its collapsed state within catheter 312. If distal protection means is a balloon, it will be connected to an inflation lumen formed in or carried by catheter 312.

Figure 19:
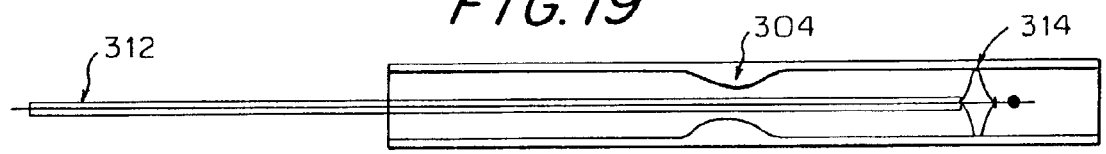

In the next step, depicted in FIG. 19, the distal protection means 314 is deployed until it extends completely across the blood flow path defined by artery 302 in order to catch all emboli particles that may be released from the lesion site upon the following steps of the procedure. Protection means 314 will stay in place until the end of the procedure.

Figure 20:
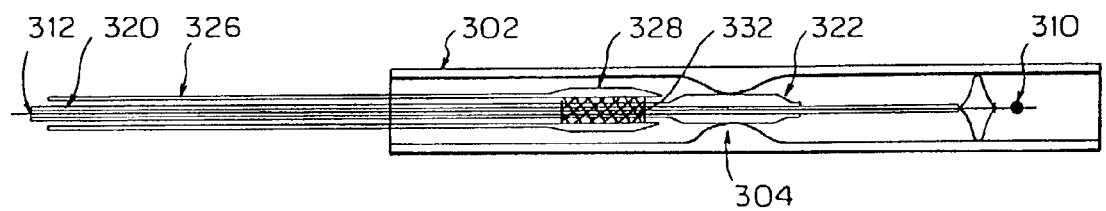

FIG. 20 shows the following step in which a predilatation catheter 320 is introduced over guiding catheter 312. Predilatation catheter 320 carries, at its distal end, a predilatation balloon 322. Predilatation catheter 320 can be advanced over guiding catheter 312 and has several purposes. First, its predilatation balloon 322 can be used to enlarge the inner diameter of lesion 304 in order to create sufficient space for positioning a post-dilatation device 326 in the form of a sheath carrying an inflatable balloon section 328. Section 328 may, if desired, carry a stent 332 that is initially in a radially contracted, or collapsed, state. Furthermore the distal tip of the catheter 320 with balloon 322 can act as an internal support for the post-dilatation balloon 328. The inner wall of device 326 constitutes a delivery sheath within which self-expanding stent 332 is retained prior to deployment and out of which stent 332 can by pushed by some conventional delivery means (not shown). Such a delivery means for self-expanding stents can be of any kind, for example a pusher-wire that pushes against the proximal side of the stent to push it out of the sheath.

Figure 21:
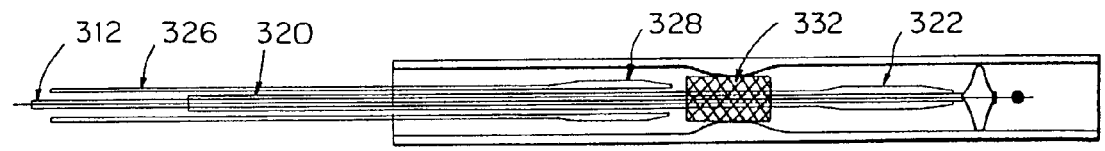

FIG. 21 shows the subsequent step in which predilatation balloon 322 has been deflated and advanced in the distal, or downstream, direction. Self-expanding stent 332 has been pushed out of delivery sheath 326. Normally, a delivery sheath only serves to bring a stent in its compressed state to the lesion site and to hold it compressed until it is to be deployed. This sheath generally has a cylindrical shape and upon delivery of the stent the sheath is pulled back, while the self-expanding stent leaves the distal tip of the delivery sheath. The sheath is then removed from the patient's body. The stent may have enough radial expansion force to fully open at the lesion site, but often this force is insufficient and the stent will stay in some intermediate semi-deployed position. A self-expanding stent can be made of several types of material, for example nitinol. Nitinol is a material with mechanical hysteresis and the force needed to collapse the stent is much higher than the radial force that the stent exerts upon deployment. This means that a nitinol self-expanding stent may be strong enough to hold an artery open, but it may need some help to reach full deployment. This help can come from post-dilatation balloon 328.

Figure 22:
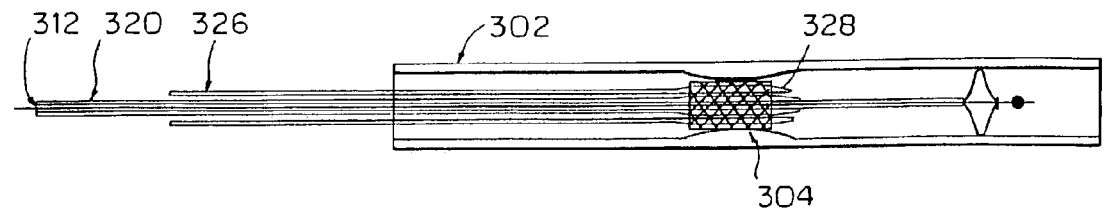
Figure 23:

FIG. 22 shows the next step in which sheath 326 is used to help deploy stent 332. The distal end of sheath 326 with balloon section 328 can be inflated through a lumen (not shown) in the sheath wall. First the delivery sheath 326 is advanced again and the balloon area 328 is lined up with stent 332 in lesion site 304. Inflation of balloon section 328 will now cause further expansion of stent 332. However, the inner wall of sheath 326 that held stent 332 before delivery may collapse under the high pressure that may be needed to fully deploy stent 332. Therefore, predilatation balloon 322 can be inflated to be used to create a stiffer inner support for sheath 326. By lining up of both balloon sections, as shown in FIG. 23, a concentric double balloon segment is created, which is strong enough for post-dilatation.

Figure 24:
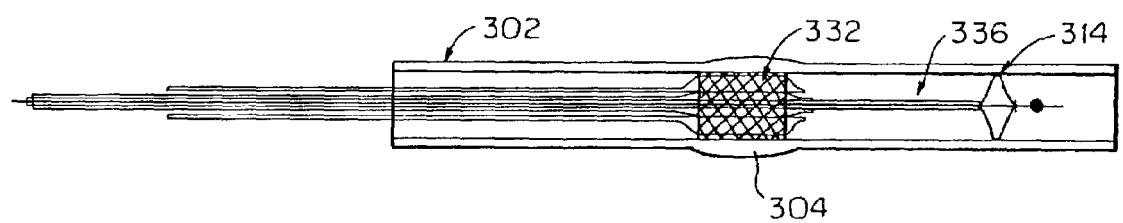

FIG. 24 show the next step in which stent 332 is fully deployed by the combined forces of balloon 322 and post-dilatation balloon section 328, despite the opposing forces of the artery wall at lesion site 304 that now has become a larger opening. If distal protection means 314 is a balloon and if balloon section 328 causes full proximal occlusion, a closed chamber 336 is created in artery 302 between balloon 314 and balloon section 328.

Figure 25:
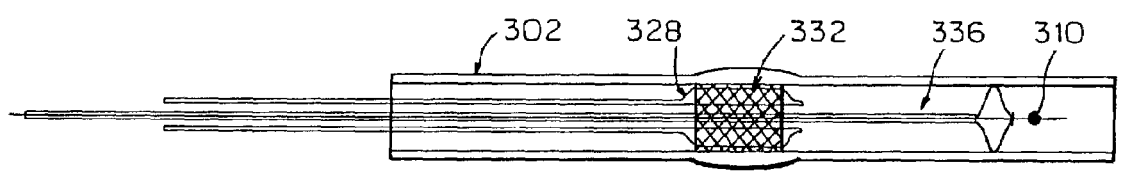
Figure 26:
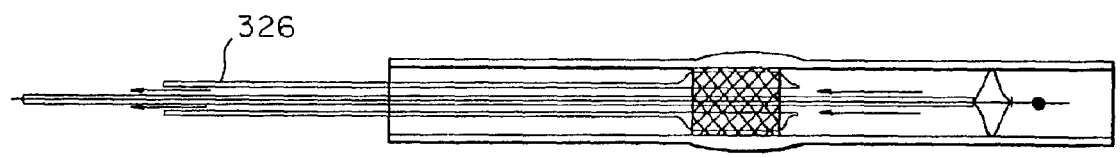

FIGS. 25 and 26 show the next step in which predilatation catheter 320 has been removed, leaving inflated balloon section 328 around delivery sheath 326 in place. Although the internal support for sheath 326 has been removed, inflated balloon section 328 can easily be used for proximal occlusion means, because the pressure may be much lower than for post-dilatation of the lesion and stent deployment. Sheath 326 that held stent 332 before can now be used as a working channel, e.g. for flushing and suction. This working channel is in open connection with devices outside of the patient's body and can be used for a series of procedures in the closed chamber 336 between balloon 314 and balloon section 328. One advantage of this closed chamber is that it can be flushed with a clear solution having a composition that can dissolve the plaque without danger for downstream body parts. Such compositions are known in the art. After flushing with a clear fluid the artery wall in the chamber region can be inspected with an endoscope or an optical fiber. This. enables visual inspection under clear sight in a closed compartment of the artery including inspection of the stent surface. As long as the pressure behind the distal occlusion device is monitored, it is a safe way to work.

If desired, the inflatable delivery sheath/suction tube 326 can be deflated, pulled back until it is proximal of the stent section and then be re-inflated to enable additional flushing, suction and inspection, while the distal occlusion device 314 is still in place.

For supply of flushing fluid, a separate lumen can be made in the wall of delivery sheath 326, running to the distal end of this sheath (not shown). Other procedures in a temporary closed chamber of an artery include ultrasonic treatment, radiation therapy and drugs delivery, among others.

Figure 27:
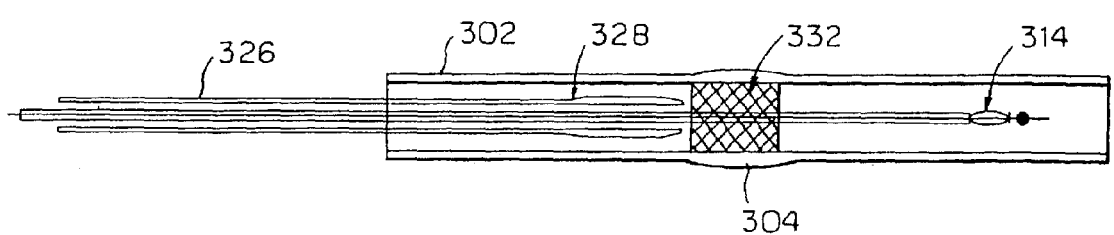

FIG. 27 shows a final step in which post-dilatation balloon section 328 has been deflated and distal protection means 314 has been collapsed. The final step can be the removal of all devices from the patient's body, except, of course, stent 332, which can stay there.

FIGS. 28–39 show filters that can serve as distal filters in the two-filter systems shown in FIGS. 1–27. However, the manufacturing techniques described below can also be used in the manufacture of proximal filters.

In the following description, filters with improved flexibility and smaller profile are described. Such a filter basically has a proximal frame for expansion and contraction and, attached thereto, a thin filter bag that is made of two basic materials. One material is the highly flexible filter membrane itself, with a pattern of holes for allowing flow of blood particles below a well defined size, and the other material is a reinforcement made of fine fibers with high axial strength but thin enough to be flexible upon bending. The reinforcement is integrated with the membrane to create a composite structure with very flexible membrane areas where the blood is filtered and extremely strong reinforcement fibers that take up excessive forces to prevent the membrane from tearing even in response to pulling forces, and act as flexible hinges at the points of attachment to the proximal frame and/or to a guide wire. All of the fibers disclosed herein can consist of, or include Dyneema® fibers, manufactured by DSM High Performance Fibers, a subsidiary of DSM N.V. These are superstrong polyethylene fibers. The fibers can also be combined with fibers or wires of other materials, such as Nitinol, to help control the expanded shape of the filter These fibers can be embedded in the membrane by a dipping or spraying process or they can be attached with glue, stitching, a solvent for the membrane material, heat, welding etc.

In order to achieve a better connection between the reinforcement fibers and the membrane material, the fibers may first be coated with a material that adheres well to the membrane material, for example with the same material as the membrane.

The fibers can be made of any strong and tough material, preferably a material with a modulus of elasticity that is higher than that of the surrounding membrane. The fibers can be made of round, flat or different shaped monofilaments or multi-filaments and can include metal elements, for example titanium or Nitinol, carbon, boron, glass, or polymers, for example ultra high molecular weight polymers with extreme tensile strength and high modulus.

The fibers not only reinforce the membrane, but also can be used to control the final geometry, prevent crack propagation, act as hinges at the place of attachment to the frame and prevent loss of the membrane or parts of it.

Because the reinforcement the membrane itself can be made much thinner than known membranes, the crossing profile of the composite filter can be much lower than for a single polymer membrane, even if the reinforcement fibers are thicker than the membrane itself.

A method according to the invention for making a reinforced filter is carried out by first providing a paraffin mold having the desired shape of the expanded, or deployed, filter bag. Then the mold is covered with a polymer skin, which will subsequently detach easily from the membrane polymer. This paraffin mold, covered with the polymer skin, is dipped in a solution of polymer and solvent until a layer of membrane polymer is created. After that step, the frame is placed around the mold and reinforcement fibers, possibly coated, are then mounted to the frame at the hinge sites and laid over the surface of the mold. Another dipping step in the solution of polymer and solvent ensures full embedding of the fibers into the growing membrane polymer layer. Finally, the perfusion hole pattern is laser drilled into the membrane and the last step is the removal of the paraffin by melting it out in warm water. The polymer skin can then be easily detached from the inside of the filter membrane and pulled out With the use of a paraffin mold it is possible to make complicated or very simple designs, because there is no need to remove a relatively large mandrel from the filter after it has been made. This would be complicated if the mandrel was for example a metal or polymer part, which had to be pulled through some openings at the proximal side.

Paraffin is of course not the only material that can be used for a mold. Any material that can be brought into the desired shape and can be dipped directly or after application an intermediate layer may be used. Examples are meltable materials or materials that easily dissolve in water, like salt or sugar crystals. Other examples are fine grains in a vacuum bag or an inflated balloon which is deflated after dipping. It is also possible, for certain filter embodiments, to use a mold that can be safely removed without being melted, dissolved, or deformed.

Fibers are also used for enabling the removal of an expandable device by pulling the device into a removal sheath.

The principles of the disclosed invention become clear from the following description of the figures. Identical parts in different figures are given the same reference number.

Figure 28:
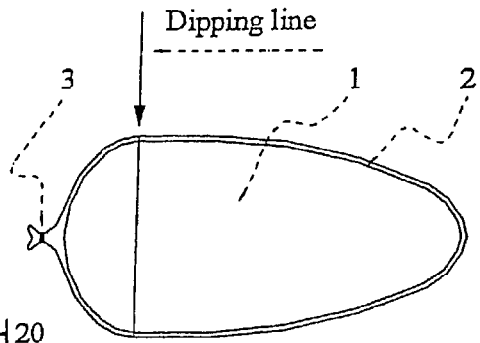
FIGS. 28–31 are side elevational views showing four stages in the fabrication of a first embodiment of a filter according to the present invention.

FIG. 28 shows a paraffin mold 401, made in the desired filter shape. Paraffin is chosen because it can be removed from the filter easily, at a temperature that does not cause degradation of the polyurethane of the filter.

However, dipping of the paraffin mold directly into the polyurethane has been found to not give the best results. Therefore, paraffin mold is first covered with a thin sheet 402 of polyvinyl alcohol. The polyvinyl alcohol is a thin sheet that can be stretched after wetting with water and pulled tight around the paraffin and then tied together with a small clip or wire 403. Then, the resulting assembly is dipped a few times in a solution of polyurethane in tetrahydrofuran, thus building a layer of polyurethane of, e.g., 3 microns in thickness at the right side of the dipping line.

Figure 29:
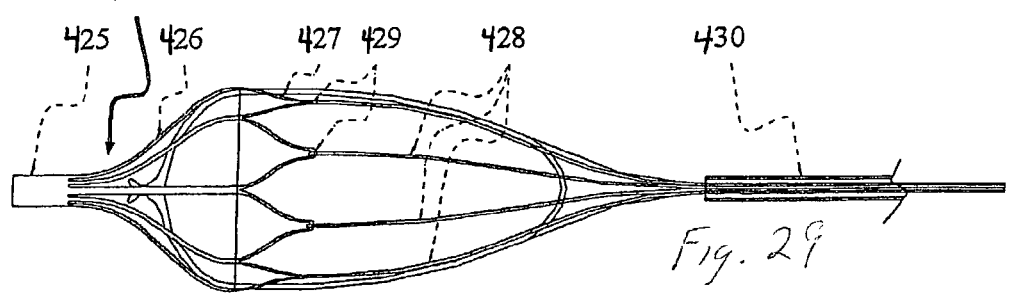

FIG. 29 shows a Nitinol frame 420 made from tubing having an outer diameter of 0.8 mm by laser cutting and shape setting. At the proximal side, which is on the left, the tube end 425 is uncut and still 0.8 mm. in diameter. From there, the tube is cut to form eight longitudinal spokes 426 that end in a zigzag section with struts 427, where the unconstrained, expanded material of frame 420 lies on a circle having a diameter is 8 mm at its largest point. This frame 420 will, at any size between the maximum diameter and the collapsed size of 0.8 mm diameter, always adapt smoothly to the given geometry of the body lumen, such as an artery. The mold of FIG. 28 is placed inside this frame and eight reinforcement fibers 428 of, for example, multifilament ultra high molecular weight polymer are attached to the most distal section of the Nitinol frame 420 at points 429. Fibers 428 can be attached to frame 420 by means of a knot or each fiber can just be run back and forth from the distal tip to the a point 429 and wrapped around the Nitinol frame at point 429. In the latter case, each fiber 428 will have twice the length shown.

At the distal end, i.e., the right-hand end, of the assembly, all fibers come together in a guide ring or tube 430, where they are held in correct position for the further dipping operation.

Figure 30:
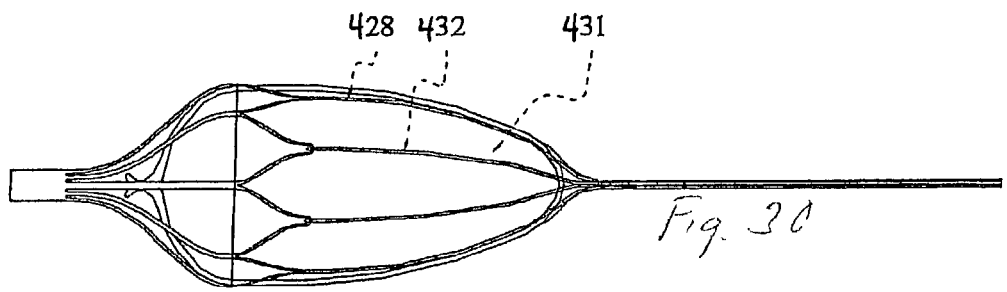

FIG. 30 shows the mold with the Nitinol frame and the surrounding fibers after having been dipped several more times until the fibers are well embedded in the polyurethane membrane, for example until the layer of polyurethane is 5 microns thick at places 431 where no reinforcement fibers 428 are present. Of course the thickness at the places 432 where these fibers are present is greater than at places 431, dependent on the type of fibers and the number of dipping steps. Guide tube 430 of FIG. 29 is removed after the dipping is finished and the membrane is dry.

Figure 31:
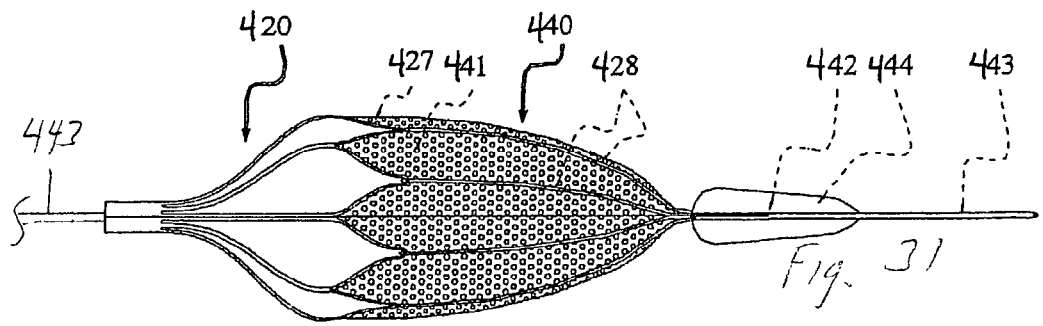

FIG. 31 shows the final filter 440, with a pattern of holes 441 each 100 microns in diameter, which have been laser drilled between the reinforcement fibers 428. After drilling of the holes, the central paraffin mold 401 is removed by melting in warm water, which can be at a temperature of 50° C. The polyvinyl alcohol layer is easily released from the polyurethane filter membrane and is removed. Further, the fibers 428 are cut to the correct length at point 442 and attached to a central guide wire 443 in a connector 444 in the form of a nose tip that fits on top of the delivery catheter if the filter is retracted into this catheter before placement into the body lumen of the patient. Note that the polyurethane membrane between the Nitinol struts 427 at the distal end of frame 420 is also removed, in the spaces enclosed by struts 427 and the dipping line, preferably by laser cutting.

This construction is extremely strong and still very flexible. The 5 micron thick membrane with the reinforcement fibers 428 fits easily in a delivery catheter of only 0.9 mm inner diameter and adapts to all sizes of arteries between 1 and 8 mm diameter.

The central guide wire 443 extends to the left from connector 444 through the membrane and frame 420, including the uncut part of tubing 425. Within connector 444, fibers 428 are wrapped around, and secured to, guide wire 443. To remove the filter from a delivery catheter, guide wire 442 is pushed from its proximal end (not shown-to the left in FIG. 31) so that a pulling force is exerted on fibers 428 due to their connection to guide wire 443 in connector 444. Thus, all tension forces on the distal section of the filter are taken up by the reinforcement fibers 428. The membrane only has to follow these fibers and unfold as soon as it leaves the catheter. The filter opens because of the elasticity of Nitinol frame 420. Also the blood pressure in the artery further helps to open the filter like a parachute. Upon bending of the filter there is almost no force needed at the sites where fibers are attached to the Nitinol struts, so these sites act as hinges. Even in strongly curved arteries the filter frame still adapts well to the artery wall and there is almost no blood leakage between the membrane and artery wall.

The fibers are so well embedded in the polyurethane membrane that in case the membrane detaches from a Nitinol frame strut, the membrane will still have a strong connection to the frame and can be collapsed and removed from the patient safely.

In case of a tear in the membrane, for example starting from a 100 micron hole, this membrane may tear further, but only until the tear meets a fiber. There the tear will stop, and the membrane can be removed safely and completely as well. Of course this situation is very undesirable and the loss of some entrapped emboli may be the consequence, but at least the removal of the filter itself would not cause problems.

After a medical procedure has been performed, the Nitinol frame can be collapsed to close the mouth of the filter and entrapped emboli cannot leave this closed filter bag anymore. The hinges guarantee now that the filled bag hangs at the distal end of the removal catheter and still can move easily through curved arteries.

The reinforcement fibers can be used not only for their high tensile strength. They can also be combined with memory metal wires, or filaments, made, for example, of Nitinol wires that can be shape set to almost any desired shape by heat treatment. Such wires may be embedded in or attached to the membrane to guarantee a smooth folding/unfolding of the membrane. An example is an embedded Nitinol wire that helps to give the mouth of the filter membrane a smooth geometry that fits well to the artery wall. Such a Nitinol wire for shape control can be combined with a more flexible, but stronger, fiber, which is used to protect the membrane against incidental overload, tear propagation or any of the described problems in non-reinforced membranes.

The orientation and number of the reinforcement fibers is not limited and can vary with the desired application.

Figure 32:
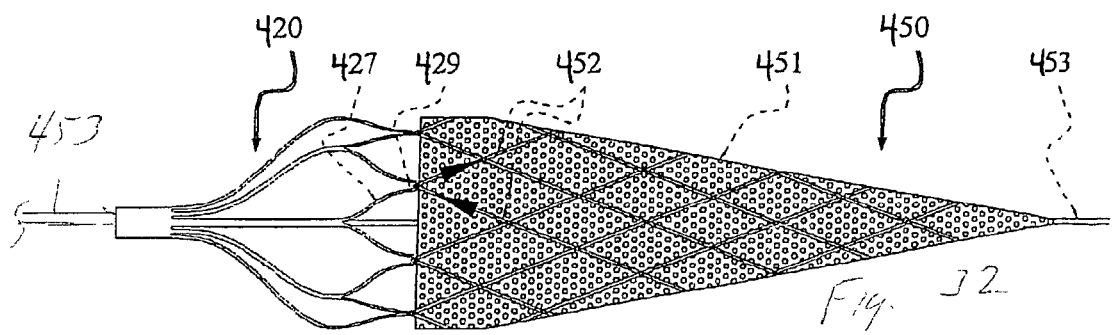
FIG. 32 is an elevational view showing a second embodiment of a filter according to the present invention.

In FIG. 32 a distal filter 450 is shown, with a conical shaped filter membrane 451, attached to the same proximal wire frame 420 as in FIGS. 29–31. In this example, however, the membrane is not attached directly to the Nitinol frame. It is attached, for example, by guiding a single, long reinforcement fiber 452 from the distal end at an angle with the cone surface until it reaches the Nitinol struts 427 at points 429, then wrapping fiber 452 around one of these struts at a point 429 and guiding the fiber back to the distal tip with a reverse angle and repeating this operation several times. Arrows in the drawing show how fiber 452 runs back and forth. By this method the use of knots at the fiber-Nitinol connection is redundant and the safety is further increased, because the filter can never detach from the frame. In this embodiment, membrane 451 can also be formed by dipping a suitably shaped mold in a solution of polymer and solvent.

A guide wire 453 is fastened to fiber 452 at at least one point at the distal end of the filter and extends through the filter to a proximal end thereof (not shown-to the left in FIG. 32).

The pattern with crossing reinforcement fibers gives the filter membrane different elastic properties and gives the benefit of an improved, but limited axial elasticity.

The pattern of filter holes, preferably cut by laser, can be made in zones between the fibers to avoid damaging the fibers.

However, if the pattern of reinforcement fibers is very fine, the holes may just be cut without regard for the locations of these fibers. There will then still be enough reinforcement left, because adjacent crossing, parallel or angled uncut fibers can take over some forces via the embedding material of the membrane itself.

The conical filter shape has the following advantages. If this filter has a maximum, expanded, diameter of 8 mm and is placed in an artery of 8 mm diameter, all holes will be free from the artery wall and blood can flow through all holes. As soon as particles of debris, like emboli, are entrapped, they will tend to collect at the most distal tip, leaving the more proximal holes open.

The area of the conical surface of the cone relates to the cross-sectional area of the artery as the length of the cone edge from base to tip relates to the radius of the artery. Preferably, the total surface area of the holes should be at least equal to the cross-sectional area of the artery in order to guarantee an almost undistorted blood flow. This is the case if the ratio of the total surface area of the cone surface to the total hole surface area is smaller than the ratio of the cone surface area to the cross-sectional area of the artery, or, in other words, the total surface are of the holes is at least equal to the cross-sectional area of the artery.

For an artery having an inner diameter of 8 mm, a total number of 6400 holes each with a 100 micron diameter is needed for the same surface area. Of course, the type of flow through small 100 micron diameter holes is different from the undistorted flow through an open artery. However, because the wall thickness of a reinforced membrane according to the invention can be extremely small, the length of a hole (for example only 5 microns) ensures a much better flow than compared to a 100 micron hole in a thick membrane.

A filter made in conical shape will also have enough free holes if it is used in arteries with smaller diameter. The holes that touch the artery wall will not contribute to the flow, but the remaining free holes still have the same surface area as the actual cross section of the smaller artery.

Filters according to this invention are so much more flexible than existing filters that they can be made longer without creating problems in strong curves. Therefore they can have greater storage capacity for emboli.

If the reinforced membrane and the filter frame are mounted to each other without overlap, as in FIG. 32, it may be clear that the collapsed diameter can be made smaller than in the case of, for example, FIG. 31.

Here, at a specific cross section of the Nitinol frame near the attachment points 429, the Nitinol frame, the membrane, the fibers and a central guide wire 453 all take their part of the available cross section in the delivery sheath. It depends on the demands if this is allowable, or if a design should be chosen without overlap, where frame and membrane are separated by the fiber hinges, thus reducing the size.

The construction of Nitinol frame 420 has certain advantages. Production of the frame is very simple, the guide wire is kept in the center, and the filter can be pulled out of the delivery sheath by pushing on guide wire 453 from the left to exert a pulling force on fiber 452 and membrane 451.

During removal of the filter from an artery, the longitudinal spokes 426 of frame 420 just have to pull the struts 427 of the zigzag section into a removal sheath.

However, such a frame can also have some disadvantages. In strongly curved arteries the guide wire will bend and it will cause forces that may deform the zigzag struts. Eventually the contact with the wall of the artery is not optimal then, which is undesirable.

Another disadvantage is that axial movements of the guide wire, for example caused by the angioplasty/stenting procedure can influence the position of the filter. It would be better if the guide wire could move freely over at least a certain axial length plus in radial and tangential directions within the entire cross section of the filter, without exerting any force on the expanded frame.

In FIGS. 33–36 an embodiment with such a freely movable guide wire is disclosed.

FIG. 33 shows a filter 460 that is constructed in such a way that it can be delivered from a delivery sheath by pushing on a guide wire 461 to exert a pulling force on the filter. After completion of use of the filter in a medical procedure, the filter is removed by pulling it into a removal sheath with the aid of guide wire 461. The pulling forces are applied in both directions by moving guide wire 461 in axial direction relative to the sheath.

Guide wire 461 runs through the filter and ends at distal section 462. Fastened to guide wire 461 are stops 463 and 464 that have a larger diameter than the guide wire itself. These stops are connected tightly to the guide wire by any known technique. At the distal tip of filter 460, a ring 465 is fastened to the filter and guide wire 461 can slide freely through ring 465, until stop 463 touches ring 465.

At the proximal side of stop 464, a second slide ring 466 is mounted around guide wire 461 to allow guide wire 461 to slide freely therethrough. Slide rings 465 and 466 are given a smooth shape with rounded edges to let the move easily in associated sheaths and in the artery.

The filter membrane 470 is connected directly to slide ring 465 and reinforcement fibers 471 are also attached tightly to ring 465. At the other side, reinforcement fibers 471 are connected to an expandable frame 480 at connection points 481, possibly together with the membrane material itself.

Expandable frame 480 is provided with points of attachment 482 at its proximal side, which are needed to pull the frame back into a removal sheath, such as sheath 490 in FIG. 34. Flexible fibers 483 are connected to these points 482 and run to the proximal slide ring 466, to which they are securely attached.

If the guide wire is moved through the filter in the proximal direction, i.e., to the left in FIGS. 33–35, stop 464 will move freely over a distance $X_1$ before it touches slide ring 466, and fibers 483 become stretched.

If the guide wire is moved through the filter in the distal direction, i.e., to the right in FIGS. 33–35, stop 463 will move freely over a distance $X_2$ before it touches slide ring 465. Fibers 483 will hang free than, because there is no axial force on slide ring 466. This means that, when the filter has been placed in an artery, guide wire 461 can move freely in the cross-sectional area of the filter frame in both radial and tangential directions without exerting any forces on this frame. Further, the guide wire can also move back and forth over a total distance X $(=X_1+X_2)$ in the longitudinal direction relative to the filter, before it influences the shape or axial position of the filter in the artery. Distance X can be changed by choosing the distance between fixed stops 463 and 464. If one of these stops is removed, distance X is maximized. Of course the distal end section 462 of guide wire 461 must then be long enough to prevent slide ring 465 from disengaging from the guide wire tip.

With the construction of slide rings 465 and 466 on guide wire 461, the guide wire can be rotated around its length axis without influencing the position and shape of the filter and its frame.

All of these degrees of freedom enable the operator to use guide wire 461 for angioplasty/stenting procedures without influencing the shape and position of the distal filter. This is extremely important.

Further, this design allows the length of Nitinol frame 480 to be shortened and thus it makes the filter more flexible and more easily usable in strongly bent arteries and arteries with limited space for the filter, in view of the high degree of flexibility of membrane 470 and fibers 471 and 483. In a strongly curved artery, guide wire 461 may even touch the inner wall of frame 480, without exerting relevant forces on the filter. Even with a strongly bent guide wire, the filter will still maintain its full contact with the artery wall and guarantee a safe functioning of the device for a wide range of artery diameters and geometries.

As can be seen from a comparison of FIG. 33 with FIGS. 31 and 32, the design of FIG. 33 gives a much smaller proximal surface of the expanded frame. In FIGS. 29–32, the Nitinol spokes 426 and the proximal side of tube section 425 have a certain surface area that reduces blood flow. This surface area is much smaller in FIG. 33, because only a few thin fibers 483 are interposed in the blood flow.

Another advantage is that debris in the blood will less likely adhere to the thin fibers than to the proximal side of parts 425 and 426 of FIGS. 29–32. Of course, an additional treatment of these fibers to reduce the tendency of blood cells to adhere thereto is helpful and is a part of this invention as well. The material for these fibers can be of any kind, and they can for example made of the same materials as the reinforcement wires for the filter membrane.

An example would be a composite fiber made of a Nitinol filament core, surrounded by a multifilament ultra high molecular weight highly oriented polymer. The Nitinol can be used to give some shape control to the wire, for example to prevent adjacent fibers from becoming entangled. The polymer multifilament, besides having high strength and low strain, can have for example anti-thrombogenic agents embedded therein.

In FIG. 34 the filter of FIG. 33 is shown in a stage in which it is being delivered from a delivery sheath 490. Sheath 490 has a wall 491 and a distal end 492. At the proximal side of the guide wire 461 a pushing force F is applied in the distal direction, while sheath 490 is being pulled back in the proximal direction, or is being held in place. Stop 463 on guide wire 461 is now in direct contact with slide ring 465, and force F is transferred by this ring to the reinforcement fibers 471 of the filter membrane 470. By the resulting pulling force in the filter membrane and fibers 471, the filter membrane is stretched and this pulling force is transferred to the collapsed frame 480 via connection points 481. The frame and filter membrane will easily slide out of sheath 490 by this pulling force, followed by the unloaded fibers 483 and slide ring 466. As can be seen, the proximal section 482 of frame 480, to which the fibers 483 are attached, is slightly bent inwards to create a conical proximal side of frame 480.

FIG. 35 shows the filter in a position to be retracted into a removal sheath 500. Removal sheath 500 has a wall 493 and a distal end 494. At distal end 494, the removal sheath may have a flared end section 495, as shown in FIG. 35a, a chamfered wall 496, as shown in FIG. 35b, or a combination thereof. Distal end 494 must enable the retrieval of the filter into the lumen of sheath 500 by a pulling force, which is applied to the proximal end of guide wire 461 while sheath 500 is being moved in the distal direction or is being held in place. The tapered proximal side 482 of the frame also assists withdrawal of the frame into removal sheath 500.

The force $F_1$, applied to guide wire 461, is transferred by stop 464 to slide ring 466, which distributes the force to fibers 483 that are now pulling on the proximal side 482 of frame 480.

The wire ends can be attached by any technique that is available, for example by putting them through respective holes 484 in frame 480, and securing them by a knot 485 on the inside surface of the frame. The proximal tips 486 of frame 480 have been formed in such a way that they are slightly curved inside with a conical top angle that is larger than the top angle of the cone, described by the stretched fibers 483, just before the parts 486 enter into removal sheath 493. This is done to prevent these proximal sections from becoming stuck at the distal end 494 of the removal sheath.

With the tapered shape of frame 480, the tension force in fibers 483 will easily make it possible to slide the removal sheath over the frame until it is completely covered by this sheath. Filter membrane 470, eventually filled with embolic debris, does not have to be pulled into this sheath completely. It can extend from the distal end 494 while the whole device is removed from the artery.

FIG. 36a and 36b are side views of an alternative embodiment 510 of the filter frame, in its expanded and collapsed shapes, respectively. This embodiment is shorter than the embodiment of FIGS. 33–35, and, in particular, lacks the distal end portion of the embodiment of FIGS. 33–35. In FIGS. 36a and 36b, frame 510 is composed of struts configured in a zigzag-pattern. Here again the proximal side 512 is curved inwardly with curved tips 516 and it has attachment holes 514 for the fibers.

The fact that the filter frame is not subjected to a pushing force during deployment from, or retraction into, a sheath enables a further downscaling of the frame struts and thus a miniaturization of the delivery profile of the device. This is also enhanced by the fact that the guide wire does not influence the shape and position of the filter upon angioplasty and stenting, so the frame itself can now also be made lighter.

In FIG. 37, another embodiment of the filter frame 520 is shown. Elongated attachment parts 526 are formed at the proximal side 512 of the frame 520 in order to bring the holes 524 for the attachment of the fibers 483 further away from the expandable and collapsible unit cells of the frame. This increased length helps to achieve a smoother shape upon shape setting, so that these struts will have the desired curvature that is needed to slide easily into the removal sheath. Placement of the attachment holes at the very proximal tip of the frame struts will also help to allow the frame to be pulled back into the removal sheath without the risk of getting stuck at the entrance of this sheath.

The elongated struts forming frame 520 can be shape set into almost any desirable angle. A part of the struts may be parallel with the length axis of the filter, while another part or parts may be angled inside or outside, as needed for smooth removal of the device. Outside angled tips may even help to anchor the frame in the blood vessel for more axial stability.

FIG. 38 shows another feature of the present invention. The design of a filter according to the invention with flexible fibers 483 makes it possible to push a tube 530 over guide wire 461 until the distal end 531 of tube 530 reaches deep into the filter.

The fibers 483 will easily move with distal end 531 of tube 530 and, dependant on the length of these fibers, the most distal position of tube end 531 can be chosen. This positioning of a tube inside or beyond the frame 520 opens the possibility of flushing and/or suction through it in order to move debris either deeper into the distal end of the filter or to suction debris out of the filter. Flushing with certain liquids can also help to make the debris smaller. An additional treatment device can also be inserted through tube 530 inside the filter. This additional treatment device can be any means for inspection, measuring or all kinds of treatments like breaking up of clots by mechanical means, laser, ultrasonics, etc. Also additional retrieval devices may be brought into the filter through tube 530. Of course, tube 530 may be the same tube as the removal sheath, in order to save components and to reduce operating time.

FIG. 39 shows another embodiment for the shape of a filter 470, with an additional reservoir 472 for storage of debris. Because the conical filters of FIGS. 33–38 have a tip with limited space to store debris, the filter may be filled too soon, which may cause problems with maintaining a satisfactory blood flow through the filter.

Normally it can be expected that the major part of the debris will collect most distally, leaving the most proximal holes open for blood flow. This can be improved by providing additional reservoir 472, which is connected to the conical section 473 by a portion 474. If the diameter of reservoir 472 is half the maximum diameter of the frame, the surface area that remains free for blood flow between the wall of the full reservoir and the artery wall is still 75% of the maximum surface area of the artery. The capacity of reservoir 472 can be chosen so that the closure of filter holes in section 473 by abundant debris is most unlikely. Additional flushing and/or suction as described with references to FIG. 38, may further help here. Of course, continuous monitoring of the blood flow beyond the distal end of the filter will give the necessary information if the situation becomes critical and the filter must be removed.

The shape and diameter of reservoir 472 will be dependent on the expected diameter and geometry of the artery that will be treated. The shape of reservoir 472 can be determined by embedded fibers. The membrane may for example be elastic, while the fibers can have a limited stretchability. Dependent on the pressure inside the reservoir, the diameter of the membrane can be made to vary until it reaches a certain predetermined value, when the embedded fibers reach their strain limit. Such embedded diameter limiting fibers will have a more or less tangential orientation.

Frames as shown in FIGS. 33–39 and described above may not only be used in application of filters. They can also be used as a removable temporary stent, dilator, reamer, occlusion device for main artery or side artery, a housing for a graft, a valve, a delivery platform for drugs, radiation or gene therapy, or any other device that has to be placed and removed after some time. Applications are not restricted to arteries, but are meant for all body lumens.

A filter according to the invention, particularly because of the flexibility of the fibers, allows an element, such as tube 530 of FIG. 38, to penetrate into the region enclosed by the membrane structure to apply suction to debris contained in the filter bag either continuously or intermittently. This is particularly applicable to the distal filter of a two filter assembly. The tube can be introduced over a guide wire associated with the filter and can enter the filter with no risk of perforating it. The safety of applying suction to the interior of the filter is ensured by the nature of the material used for the membrane and reinforcing fibers, as described above with reference to FIGS. 28–29. Such suction allows the filter to be maintained relatively free of debris and helps to achieve a relative stability in blood flow through the membrane. In addition, the suction element enables the filter to be kept in a relatively empty condition prior to its being closed and withdrawn and prior to the use of a distal retrieval filter.

Membranes according to the invention can be used, wit or without holes, or pores, as skin for grafts, stents, heart valve tissues, etc.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system for preventing embolism and microembolism in a vascular system, said system comprising:
   a guiding catheter having an outer surface;
   a blocking balloon carried by said guiding catheter on said outer surface
   an elongated support element arranged to extend through, and beyond, said guiding catheter;
   a first filter element with millipores carried by said support element and radially expandable from a closed condition to an open condition;
   a second filter element surrounding said support element and radially expandable from a closed condition to an open condition; and
   means coupled to at least one of said filter elements for moving said at least one of said filter elements between its respective closed and open conditions independently of movements of the other one of said filter elements between its respective closed and open conditions,
   wherein:
      each of said filter elements has an open front end constituting a passage through which particles pass into said filter element, a bottom end remote from said front end and a filter surface structured to prevent passage of particles and permit passage of blood;
      said first filter element has a conical shape with an apex at said bottom end, or a basket shape that is closed at said bottom end;
      said elongated support element is secured to said bottom end of said first filter element;
      said second filter element has a periphery delimiting said open front end and a central opening at said bottom end, spaced inwardly from said periphery; and
      said elongated support element extends through said central opening in said second filter element.

2. A system for preventing embolism and microembolism in a vascular system, said system comprising:
   an elongated support element;
   a first filter element with millipores carried by said support element and radially expandable from a closed condition to an open condition;
   a second filter element surrounding said support element and radially expandable from a closed condition to an open condition; and
   means coupled to at least one of said filter elements for moving said at least one of said filter elements between its respective closed and open conditions independently of movements of the other one of said filter elements between its respective closed and open conditions,
   wherein
      each of said filter elements has a filter surface structured to prevent passage of particles and permit passage of blood;
      at least one of said filter elements comprises:
      an armature constituted by a mesh or screen made of a resiliently deformable material, said armature having surface;
      and a sheet of polymer filter material secured to, and covering the surface of, said armature and providing said filter surface;
      said first filter element has a conical shape with an apex or a basket shape with a closed bottom;
      said elongated support element is secured to said apex or said bottom of said first filter element;
      said second filter element has a periphery and a central opening spaced inwardly from said periphery; and
      said elongated support element extends through said central opening in said second filter element.

3. A system for preventing embolism and microembolism in a vascular system, said system comprising:
   an elongated support element;
   a first filter element with millipores carried by said support element and radially expandable from a closed condition to an open condition;
   a second filter element surrounding said support element and radially expandable from a closed condition to an open condition; and
   means coupled to at least one of said filter elements for moving said at least one of said filter elements between its respective closed and open conditions independently of movements of the other one of said filter elements between its respective closed and open conditions, wherein:
each of said filter elements has a filter surface structured to prevent passage of particles and permit passage of blood; and
one of said filter elements comprises:
an armature made of a resiliently deformable material and having an open end;
a sheet of polymer filter material secured to said armature and providing said filter surface;
a flexible additional filter sheet having a periphery secured to the open end of said armature; and
a wire attached to said flexible additional filter sheet at a point spaced inwardly from said periphery and extending to a point outside of the vascular system, said wire being movable at the point outside of the vascular system to alter the shape of said flexible additional filter sheet.

4. The system according to claim 3, wherein said flexible additional filter sheet has filter holes dimensioned to prevent passage of particles that pass through said sheet of polymer filter material of said one of said, filter elements.

5. The system according to claim 4, wherein said one of said filter elements is said first filter element.

* * * * *